(12) United States Patent
Buelow

(10) Patent No.: US 8,907,157 B2
(45) Date of Patent: *Dec. 9, 2014

(54) METHODS FOR PRODUCING TRANSGENIC RODENTS HAVING RECOMBINANT IMMUNOGLOBULIN LOCI

(75) Inventor: Roland Buelow, Palo Alto, CA (US)

(73) Assignee: OMT, Inc., San Carlos, CA (US)

( * ) Notice: Subject to any disclaimer, the term of this patent is extended or adjusted under 35 U.S.C. 154(b) by 409 days.

This patent is subject to a terminal disclaimer.

(21) Appl. No.: 12/701,464

(22) Filed: Feb. 5, 2010

(65) Prior Publication Data

US 2010/0212035 A1    Aug. 19, 2010

Related U.S. Application Data

(63) Continuation-in-part of application No. 12/130,818, filed on May 30, 2008, now Pat. No. 8,703,485.

(60) Provisional application No. 60/941,619, filed on Jun. 1, 2007, provisional application No. 61/044,324, filed on Apr. 11, 2008.

(51) Int. Cl.
*A01K 67/00* (2006.01)
*C12N 15/00* (2006.01)

(52) U.S. Cl.
USPC .............................................. 800/18; 800/21

(58) Field of Classification Search
USPC ................... 435/325; 800/8, 18, 21
See application file for complete search history.

(56) References Cited

U.S. PATENT DOCUMENTS

| | | | |
|---|---|---|---|
| 5,574,205 A * | 11/1996 | Kucherlapati et al. | 800/3 |
| 5,939,598 A * | 8/1999 | Kucherlapati et al. | 800/25 |
| 6,075,181 A * | 6/2000 | Kucherlapati et al. | 800/25 |
| 6,114,598 A * | 9/2000 | Kucherlapati et al. | 800/18 |
| 6,139,835 A * | 10/2000 | Kucherlapati et al. | 424/93.21 |
| 6,150,584 A * | 11/2000 | Kucherlapati et al. | 800/18 |
| 6,162,963 A * | 12/2000 | Kucherlapati et al. | 800/18 |
| 6,514,752 B1 * | 2/2003 | Kucherlapati et al. | 435/320.1 |
| 6,528,313 B1 | 3/2003 | Le Mouellic | |
| 6,528,314 B1 | 3/2003 | Le Mouellic | |
| 6,657,103 B1 * | 12/2003 | Kucherlapati et al. | 800/6 |
| 6,673,986 B1 * | 1/2004 | Kucherlapati et al. | 800/18 |
| 6,713,610 B1 * | 3/2004 | Kucherlapati et al. | 530/388.23 |
| 7,064,244 B2 * | 6/2006 | Jakobovits et al. | 800/18 |
| 7,098,031 B2 * | 8/2006 | Choulika et al. | 435/455 |
| 7,129,084 B2 * | 10/2006 | Buelow et al. | 435/320.1 |
| 7,585,668 B2 * | 9/2009 | Buelow et al. | 435/320.1 |
| 2003/0017534 A1 * | 1/2003 | Buelow et al. | 435/69.1 |
| 2004/0158880 A1 * | 8/2004 | Buelow et al. | 800/6 |
| 2005/0064474 A1 | 3/2005 | Urnov | |
| 2005/0153392 A1 * | 7/2005 | Buelow et al. | 435/69.1 |
| 2005/0229263 A1 * | 10/2005 | Buelow | 800/8 |
| 2006/0026696 A1 * | 2/2006 | Buelow et al. | 800/6 |
| 2006/0117398 A1 * | 6/2006 | Buelow et al. | 800/14 |
| 2006/0153826 A1 * | 7/2006 | Arnould et al. | 424/94.61 |
| 2006/0206949 A1 * | 9/2006 | Arnould et al. | 800/14 |
| 2008/0209587 A1 * | 8/2008 | Liljedahl et al. | 800/278 |

FOREIGN PATENT DOCUMENTS

| | | | |
|---|---|---|---|
| WO | WO98/24893 | * | 6/1998 |
| WO | WO 98/24893 | | 11/1998 |
| WO | WO 02/12437 | | 2/2002 |
| WO | WO02/12437 | * | 2/2002 |
| WO | WO 03/047336 A2 | | 6/2003 |
| WO | 2004/067736 A2 | | 8/2004 |
| WO | 2005/014650 A2 | | 2/2005 |
| WO | WO 2005/038001 | | 4/2005 |

OTHER PUBLICATIONS

Porteus (Nature Biotech, Aug. 2005, vol. 23, No. 8, p. 967-973.*
Vasquez (PNAS, Jul. 17, 2001, vol. 98, No. 15, p. 8403-8410).*
Donoho (Mol. Cell. Biol., Jul. 1998, vol. 18, No. 7, p. 4070-4078).*
Cohen-Tannoudji (1998, Mol. Cell. Biol. vol. 18, p. 1444-1448).*
Pabo (Annual Rev. Biochem., 2001, vol. 70, p. 313-340).*
Isalan (Methods in Enzymology, 2001, vol. 340, p. 593-609).*
Geurts (Science, 2009, vol. 325, p. 433).*
Argast et al. (1998) J. Mol. Biol. 280, 345-353.
Buelow et al. (2006) Human Antibodies 15:19-23.
Capecchi (1989) Science 244:1288-1292.
Chen and Zhao (2005) Nucleic Acid Research 33(18):e154.
Choulika et al. (1995) Mol. Cell. Biol. 15:1968-1973.
Cohen-Tannoudji (1998) Mol. Cell. Biol. 18:1444-1448.
Donoho et al. (1998) Mol. Cell. Biol. 18:4070-4078.
Geurts et al. (2009) Science 325:433.
Jakobovits et al. (2007) Nature Biotechnology 25: 1134-1143.
Johnson et al. (2001) Biochem. Soc. Trans. 29:196-201.
Kitamura and Rajewky (1992) Nature 356:154-156.
Liu et al. (2001) J. Biol. Chem. 276:11323-11334.
MacPherson et al. (2001) Nature Immunology 2(7):625-631.
Mendez et al. (1997) Nature Genetics 15:146-156.
Moehle et al. (2007) PNAS 104:3055-3060.
Nguyen et al. (2003) Immunology 109:93-101.
Porteus et al. (2005) Nature Biotechnology 23:967-973.
Rouet et al. (1994) Mol. Cell. Biol. 14:8096-8106.
Smith et al. (2006) Nucleic Acids Research vol. 34.
Van Keuren et al. (2009) Transgenic Res. 18(5); 769-85 Epub Apr. 26, 2009.
Vasquez (2001) PNAS 98:8403-8410.
Beumer et al. (2008) PNAS 105:19821-19826.
McConnel Smith et al. (2009) PNAS 106:5099-5104.
Ohbayashi et al. (2005) PNAS 102:13628-13633.
Townsend et al. (2009) Nature 459:442-445.
Gorman, S D, "Reshaping a Therapeutic CD4 Antibody," Proc. Natl. Acad. Sci. USA, 88 (10):4181-85 (1991).

(Continued)

*Primary Examiner* — Michael C. Wilson

(57) ABSTRACT

The invention provides methods for the production of transgenic animals comprising a recombinant Ig locus, as well as transgenic antibodies derived therefrom. The methods involve meganuclease cleavage-stimulated homologous recombination in mammalian embryos.

10 Claims, 7 Drawing Sheets

(56) References Cited

OTHER PUBLICATIONS

Janssens, et al., "Generation of heavy-chain-only anitibodies in mice", PNAS 103 (41):15130-15135 (2006).

Zarrin, Ali A, et al., "Antibody class switching mediated by yeast endonuclease-generated DNA breaks," Science, 315 (5810):377-81 (2007).

* cited by examiner

Figure 2. Interaction of I-SceI and DNA at 3' end of recognition sequence

Figure 3. Interaction of the 5' end of the I-SceI recognition sequence with I-SceI.

Figure 4. Sequence recognition mechanism of I-CreI

Figure 5. Schematic diagram of the strategy for altering recognition sequence of I-CreI.

Figure 7 gtaacctgagctgaactggaaagagatgtactggataaccttaactgggctgagatgagctaggtctacccaggcctggatcagcttaattagg
gtaggctagaccaaactgtagcagtatgtattagcctgtgccaagctgggctacattaaactaaactggacttagctaggctcagattagtttcgc
tactctagatggggtaagttgggccaaactgggatgaactaatttaactagcctgagatgggcagatctgaagtgtagcaaacacagccagg
gtgaactgaatgagtttgaccaggcctggaccagttaggctaaggaccttgtcctgggcagaccgtgtgctatggtggagtttcatgatgatgcc
ataagagttcccccaccataacccacgtttctcctaccccatatacctgtctggtgtgtaaacctaatctttgtgtgctgatacagaagcctgagcc
catcccccttccaccaccacctacctattgctttggaatgagcaaggttatctcagcgaatgtctcaaagggaagccgggacctaggcctgtcc
ctgagagcagatgttcatgccctggagtggctgccggtggctgaagggccagaaccacctactctagaggcatctctcgctgtctgtgaagtc
ttccaaagacattcctgtggttagaaggcagccctgctgtggctctgtcccatagaccaaacttacctactatctagtcctgccaaccttaagagc
agcaacatggagacagcagagtgtagagagatctcctgactggcaggaggcaagaagatggattcttactcgtccatttctctttatccctctct
ggtcctcagGGAGTGCATCCGCCCCAACCCTTTTCCCCCTCGTCTCCTGTGAGAATTCCCCGTCGGA
TACGAGCAGCGTGGCCGTTGGCTGCCTCGCACAGGACTTCCTTCCCGACTCCATCACTTTCTCC
TGGAAATACAAGAACAACTCTGACATCAGCAGCACCCGGGGCTTCCCATCAGTCCTGAGAGGGG
GCAAGTACGCAGCCACCTCACAGGTGCTGCTGCCTTCCAAGGACGTCATGCAGGGCACAGACG
AACACGTGGTGTGCAAAGTCCAGCACCCCAACGGCAACAAAGAAAAGAACGTGCCTCTTCCAGgt
aagaaccaacccttcccgaggggatggggagaggggcaggcccaggcatggcccagagggagcagtcgactgggtcttaagccagcc
tgagctcacacctcaacctttcattccagctgtcgttgagatgaaccccaatgtgagtgtgttcattccaccacgtgatgccttctctggccctgcac
cccgcaagtccagactcatctgcgaggccaccaacttcagtcccaaacagatcacagtatcctggctacaggatgggaagcctgtgaaatct
ggcttcaccacagagccagtgactgtcgaggccaaaggatccagaccccaaacctacaaggtcataagcacactgaccatcactgaaagc
gactggctgaacctgaatgtgttcacctgccgcgtggatcacaggggtctcaccttctggaagaacgtgtcctccacatgcgctgccagtgagt
agcctgtgctaagcccaatgcctagccctcccacattagagcagtcctcctacggttgtggccaatgccacccagacatggtcatttgcttcttga
gccttggcttccaacagtggccaaggccaaggatgagcagtaggcagcaggggggatgagagtcagatggagggaatcagcatcttcccta
agcagatttggaagatggagactgagcttttatccaacttcacaactagacacatcacaacctaacacagtgttctcttgactgcaggtccatcta
cagacatcctagccttcccatcccccctcctttgctgacatcttcctcaccaagtctgctaagctgtcctgtctggtcacaaacctggcaacctat
gacaccctgaatatctcctggtcttccaaaagtggtgaaccactggagaccaacactaaaatcatggaaagtcaccccaatggcaccttcagt
gctgtgggtgtggctagtgtttgtatggaagactgggataacaggaaggaatttgtatgcactgtgactcacagggacctgccttcaccacaga
aaaaattcatctcaaaacccaatggtaggtatccccctttccttcccctccaattccagagcatacctgtacctcacagggagggcaggtcccc
ttctaccctatcctcactattatctttgcttacagagagtggccaaacatccacctgctgtgtacctgctgccgccagcccgtgaacaactgatcctga
gggagtcggccacagtcacctgcctggtgaagggtttctctcctgcagacatctttgtacagtggcttcagagagggcaacccttgtcctcagac
aagtatgtgaccagtgccccaatgccagagcctggggctccaggcctgtacttcacccacagcatcctgactgtgacagaggaggaatgga
actccggagagacctacacctgtgttgtaggccacgaggccctgccacacatg

METHODS FOR PRODUCING TRANSGENIC RODENTS HAVING RECOMBINANT IMMUNOGLOBULIN LOCI

CROSS-REFERENCE TO RELATED APPLICATIONS

This application is a continuation-in-part of U.S. Ser. No. 12/130,818 filed 30 May 2008, which claims priority to U.S. provisional patent application U.S. Ser. No. 60/941,619 filed 1 Jun. 2007, and U.S. provisional patent application U.S. Ser. No. 61/044,324 filed 11 Apr. 2008. Each of these applications is incorporated herein in its entirety by reference.

FIELD

The invention relates to transgenic animals comprising recombinant Ig loci and methods of making the same using meganuclease cleavage-stimulated homologous recombination. The invention further relates to methods for producing transgenic antibodies, and transgenic antibodies so produced.

BACKGROUND

Antibodies are an important class of pharmaceutical products that have been successfully used in the treatment of various human diseases and conditions, including infectious diseases, cancer, allergic diseases, and graft-versus-host disease, as well as in the prevention of transplant rejection.

For many applications, it is desirable to alter the amino acid sequence of antibodies produced in particular animals. For example, one problem associated with the therapeutic application of non-human immunoglobulins is the potential immunogenicity of the same in human patients. In order to reduce the immunogenicity of such preparations, various strategies for the production of partially human (humanized) and fully human antibodies have been developed. One approach involves altering the sequence of the endogenous immunoglobulin locus in the antibody producing non-human animal in order to generate transgenic antibodies. The ability to produce transgenic antibodies having a human idiotype in non-human animals is particularly desirable as antigen binding determinants lie within the idiotype region, and non-human idiotypes are thought to contribute to the immunogenicity of antibody therapeutics. Human idiotype is an especially important consideration in respect of monoclonal antibody therapeutics, which consist of a single idiotype delivered at relatively high concentration as opposed to the variety of idiotypes delivered at lower concentrations by a polyclonal antibody mixture.

Attempts have been made to alter genomic sequences in cultured cells by taking advantage of the natural phenomenon of homologous recombination. See, for example, Capecchi (1989) Science 244:1288-1292; U.S. Pat. Nos. 6,528,313 and 6,528,314. If a polynucleotide has sufficient homology to the genomic region containing the sequence to be altered, it is possible for part or all of the sequence of the polynucleotide to replace the genomic sequence by homologous recombination. However, the frequency of homologous recombination under these circumstances is extremely low. Moreover, the frequency of insertion of the exogenous polynucleotide at genomic locations that lack sequence homology typically exceeds the frequency of homologous recombination by several orders of magnitude.

The introduction of a double-strand break into genomic DNA, in the region of the genome bearing homology to an exogenous polynucleotide, has been shown to stimulate homologous recombination at this site by several thousand-fold in cultured cells. Rouet et al. (1994) Mol. Cell. Biol. 14:8096-8106; Choulika et al. (1995) Mol. Cell. Biol. 15:1968-1973; Donoho et al. (1998) Mol. Cell. Biol. 18:4070-4078. See also Johnson et al. (2001) Biochem. Soc. Trans. 29:196-201; and Yanez et al. (1998) Gene Therapy 5:149-159. In these methods, DNA cleavage in the desired genomic region was accomplished by inserting a recognition site for a meganuclease (i.e., an endonuclease with a recognition sequence that is so large it does not occur, or occurs only rarely, in the genome of interest) into the desired genomic region.

Meganuclease cleavage-stimulated homologous recombination using naturally occurring meganucleases relies on either the fortuitous presence of, or the directed insertion of, a suitable meganuclease recognition site in the vicinity of the genomic region to be altered. Since meganuclease recognition sites are rare or nonexistent in a typical mammalian genome, and insertion of a suitable meganuclease recognition site is plagued with the same difficulties associated with other genomic alterations, methods employing conventional meganucleases have not found widespread use.

The engineering of meganucleases with novel specificities has expanded the applicability of meganuclease cleavage-stimulated homologous recombination. For example, see US 20050064474; and Moehle et al., PNAS, 104:3055-3060, 2007. However, many potential limitations to the application of cleavage-stimulated homologous recombination remain and may preclude its use in certain cell types, such as single cell mammalian embryos.

Mammalian embryos are highly sensitive to manipulation, and any damage incurred at this stage of development can have profound consequences. Accordingly, the use of cleavage-stimulated homologous recombination in mammalian embryos faces several obstacles. The introduction of nucleic acids into the pronuclei of embryos can be toxic, with embryo survival inversely correlated to the amount of nucleic acid introduced (For example, see "Generating transgenic mice from bacterial artificial chromosomes: transgenesis efficiency, integration and expression outcomes." ML Van Keuren, G B GGavrilina, W E Filipiak, M G Zeidler, T L Saunders. *Transgenic Res.* 2009 October; 18(5):769-85. Epub 2009 Apr. 26). In addition, cleavage of chromosomal DNA by meganucleases has the potential to cause chromosomal instability in any cell type.

Combining detrimental manipulations in mammalian embryos in particular could result in a high frequency of death, rendering cleavage-stimulated homologous recombination impracticable in embryos. The developmental program by which a mammalian embryo grows into a viable fetus is dependent on complex genetic and epigenetic processes involving hundreds, if not thousands, of genes and non-coding RNAs. The success of embryonic development is dependent on not only the proper quantitative regulation of each involved transcriptional unit, but their proper timing and coordinated expression. For a mammalian embryo which is embarking on the pathway to development into a viable fetus, it is not possible to extrapolate data on the effect or toxicity of nucleic acid introduction and chromosome cleavage in a cultured cell model to predict the effect on embryonic development.

Thus, the stress associated with chromosome cleavage and nucleic acid introduction suggests that cleavage-stimulated homologous recombination may be impracticable in embryos. In addition, success in gene targeting by homologous recombination may be subject to the epigenetic status of the locus containing the target site, which may vary between cell types and stages of development.

SUMMARY OF INVENTION

In one aspect, the invention provides compositions and methods for the targeted integration of a donor polynucleotide at an Ig locus in the genome of a mammalian embryo. In one embodiment, the donor polynucleotide comprises an insertion sequence that is integrated into the Ig locus. In another embodiment, the donor polynucleotide lacks an insertion sequence and provides for the deletion of sequence from an Ig locus in the genome of a mammalian embryo.

The invention stems in part from the finding that mammalian embryos can tolerate breaks in chromosomal DNA induced by meganucleases, combined with pronuclear nucleic acid microinjection, and carry on to develop into viable, fertile animals. Further, a meganuclease-induced chromosomal break in a mammalian embryo can be repaired by homologous recombination, and the homologous recombination mechanism may be exploited for targeted integration of a donor polynucleotide or targeted deletion of an endogenous Ig sequence. As demonstrated herein, immunoglobulin loci in particular are amenable to such manipulation in mammalian embryos. The transgenic animals generated by homologous recombination at an Ig locus in a single cell embryo are fertile and can transmit a recombinant Ig locus to progeny. Moreover, the subject methods provide for the production of recombinant Ig loci in mammals that have not previously been amenable to homologous recombination.

Further, using the present methods, homologous recombination is observed in embryos at a frequency that is an order of magnitude greater than that achieved in cell culture. This high frequency is sufficient to obviate the transgene integration screening step typically required with homologous recombination, and which could be detrimental to embryo survival and development.

The methods of the invention comprise the use of a meganuclease to generate a single- or double-strand break at or proximal to a chromosomal Ig locus of an embryo to stimulate integration of a donor polynucleotide by homologous recombination. Homologous recombination is effected by the use of a donor polynucleotide, which comprises two homology arms that are nucleotide sequences homologous to genomic DNA sequences, at least one of which is proximal to the meganuclease cleavage site. In one embodiment, the donor polynucleotide comprises an insertion sequence that is flanked by the nucleotide sequences homologous to genomic DNA sequences. In another embodiment, the donor polynucleotide lacks this intervening sequence.

A meganuclease can be engineered to bind any sequence in or proximal to an Ig locus and introduce a single- or double-strand break at that location. Such cleavage stimulates integration of a donor polynucleotide at or proximal to the cleavage site by homologous recombination.

In embodiments wherein the donor polynucleotide comprises an insertion sequence, the insertion sequence can comprise any nucleic acid sequence. In one embodiment, the insertion sequence comprises the nucleotide sequence of a human Ig locus or portion thereof. In one embodiment, the integration site is selected in order to replace a portion of an endogenous Ig locus or portion thereof with the insertion sequence. The insertion sequence may advantageously comprise at least one human V gene segment, at least one human J gene segment, at least one human D gene segment, at least one human C gene segment, a plurality of such segments, and the like.

In embodiments wherein the donor polynucleotide lacks an insertion sequence, the donor polynucleotide may be used to delete a portion of an endogenous Ig locus.

Accordingly, in one aspect, the invention provides transgenic animals comprising at least one recombinant Ig locus.

In one embodiment, the recombinant Ig locus produced by homologous recombination lacks a portion of an endogenous Ig locus, In one embodiment, the recombinant Ig loci produced by homologous recombination comprise at least one human Ig gene segment.

In one embodiment, a recombinant Ig locus comprises at least one human V gene segment.

In one embodiment, a recombinant Ig locus comprises at least one human J gene segment.

In one embodiment, a recombinant Ig locus comprises at least one human D gene segment.

In one embodiment, a recombinant Ig locus comprises at least one human C gene.

In a preferred embodiment, a recombinant Ig locus comprises a plurality of human Ig gene segments. Especially preferred are recombinant loci comprising a plurality of human V gene segments.

In one embodiment, a transgenic animal comprises at least one recombinant Ig heavy chain locus.

In one embodiment, a transgenic animal comprises at least one recombinant Ig light chain locus.

In one embodiment, a transgenic animal comprises at least one recombinant Ig heavy chain locus and at least one recombinant Ig light chain locus.

The recombinant Ig loci are preferably functional and capable of undergoing gene rearrangement and producing a repertoire of immunoglobulins, including transgenic immunoglobulins, in the transgenic animal. In a preferred embodiment, the transgenic animal is capable of producing transgenic antibodies having a human idiotype.

The transgenic animals are mammals. Preferred mammals include but are not limited to rodents (e.g., rats, hamsters and guinea pigs), weasels (e.g., ferrets), rabbits, farm animals, lamas, camels, and the like.

In one aspect, the invention provides methods for producing a transgenic antibody encoded by a recombinant Ig locus. The methods comprise targeted integration of a donor polynucleotide into an Ig locus of a mammalian embryo by meganuclease cleavage-stimulated homologous recombination, and expression of the Ig locus to produce transgenic antibodies.

In one aspect, the invention provides transgenic antibodies produced by transgenic animals comprising a recombinant Ig locus produced according to the subject methods. In one embodiment, a transgenic antibody has a human idiotype.

In one embodiment, polyclonal antisera comprising a transgenic antibody are provided. In one embodiment, monoclonal transgenic antibodies are provided.

In one aspect, the invention provides methods for making hybridomas capable of producing a transgenic antibody. The methods comprise the use of cells derived from transgenic animals of the invention.

In one aspect, the invention provides hybridomas so produced.

In one aspect, the invention provides isolated nucleic acids encoding transgenic monoclonal antibodies.

In one aspect, the invention provides fully human transgenic monoclonal antibodies.

In one aspect, the invention provides recombinant nucleic acids encoding fully human transgenic monoclonal antibodies.

In one aspect, the invention provides cells derived from transgenic animals of the invention. In a preferred embodiment, the invention provides cells derived from the spleen of transgenic animals of the invention. In a preferred embodiment, the invention provides B cells derived from transgenic animals of the invention, which B cells are capable of producing transgenic antibodies.

In one aspect, the invention provides pharmaceutical compositions comprising transgenic antibodies of the invention.

In one aspect, the invention provides methods of treating a patient in need of treatment, comprising administering a therapeutically effective amount of a pharmaceutical composition of the invention to the patient.

BRIEF DESCRIPTION OF THE DRAWINGS

FIG. 7. BstEll fragment containing an exon encoding human IgM CH1 (in capital letters) and rat flanking sequences.

DETAILED DESCRIPTION

Figure 1:
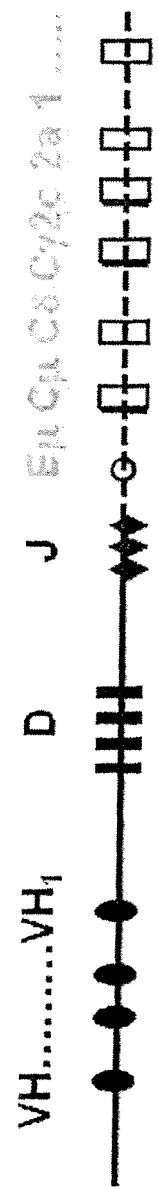
FIG. 1 shows a schematic representation of an artificial heavy chain consisting of a human V-, D, and J-region, a rat intronic enhancer and several artificial constant region genes. Artificial constant region genes contain exons encoding a human CH1 domain and rat CH 2,3 and 4 domains. Membrane spanning and cytoplasmic polypeptide sequences are encoded by rat exons.

Practice of the methods, as well as preparation and use of the compositions disclosed herein employs, unless otherwise indicated, conventional techniques in molecular biology, biochemistry, chromatin structure analysis, computational chemistry, cell culture, recombinant DNA technology and related fields, as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

The terms "nucleic acid," "polynucleotide," and "oligonucleotide" are used interchangeably and may refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; e.g., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding", for example as between a meganuclease and chromosomal DNA, refers to a sequence-specific, non-covalent interaction between macromolecules. Not all components of a binding interaction need to be sequence-specific (e.g., contacts with phosphate residues in a DNA backbone), as long as the interaction as a whole is sequence-specific.

"Homologous recombination" refers to a specialized form of DNA repair that occurs, for example, during repair of DNA single- or double-strand breaks in cells. This process requires nucleotide sequence homology between a recipient DNA molecule that is modified, and a donor DNA molecule, and uses the donor molecule to template "repair" the recipient molecule (e.g., the one that has sustained a single- or double-strand break). This leads to the transfer of genetic information from the donor molecule to the recipient molecule. Homologous recombination and its properties are well known to those of skill in the art. See, for example, Gilbert, S. F., Developmental Biology. 8th ed. 2006, Sunderland, Mass.: Sinauer associates; Lewin, B., Genes IX. Vol. IX. 2008, Sudbury, Mass.: Jones and Bartlett; Phillips, E. R. and P. J. McKinnon, DNA double-strand break repair and development. Oncogene, 2007, 26(56): p. 7799-808.

"Cleavage" of DNA refers to the breakage of one or both covalent backbones of a double-stranded DNA molecule. Single-strand breaks are sometimes referred to herein as "nicks".

A "chromosome," is a chromatin complex. A mammalian chromosome comprises a portion of the genome of a mammalian cell.

"Chromatin" is the nucleoprotein structure of the cellular genome. Cellular chromatin comprises nucleic acid, primarily DNA, and protein, including histones and non-histone chromosomal proteins.

By "recombinant immunoglobulin (Ig) locus" is meant an Ig locus that lacks a portion of the endogenous Ig locus and/or comprises at least one fragment that is not endogenous to the Ig locus in the subject mammal. Such a fragment may be human or non-human, and may include any Ig gene segment or portion thereof, or may constitute the entire Ig locus. A recombinant Ig locus is preferably a functional locus capable of undergoing gene rearrangement and producing a repertoire of immunoglobulins in the transgenic animal. Recombinant Ig loci include recombinant Ig light chain loci and recombinant Ig heavy chain loci. Once incorporated into the genome of a host, an artificial Ig locus may be referred to as a recombinant Ig locus.

By "transgenic antibody" is meant an antibody encoded by a recombinant Ig locus and produced by or otherwise derived from a transgenic mammal comprising the recombinant Ig locus in accordance with the invention. A transgenic antibody derived from a subject transgenic mammal includes a transgenic antibody produced using an isolated cell or nucleic acid obtained from the subject transgenic animal, or using a cell or nucleic acid derived from an isolated cell or nucleic acid obtained from the subject transgenic animal. In a preferred embodiment, a transgenic antibody comprises an amino acid sequence encoded by an integrated donor polynucleotide or portion thereof.

By "human idiotype" is meant a polypeptide sequence epitope present on a human antibody in the immunoglobulin heavy and/or light chain variable region. The term "human idiotype" as used herein includes both naturally occurring sequences of a human antibody, as well as synthetic sequences substantially identical to the polypeptide found in naturally occurring human antibodies. By "substantially" is meant that the degree of amino acid sequence identity is at least about 85%-95%. Preferably, the degree of amino acid sequence identity is greater than 90%, more preferably greater than 95%.

By a "chimeric antibody" or a "chimeric immunoglobulin" is meant an immunoglobulin molecule comprising amino acid sequences from at least two different Ig loci, e.g., a transgenic antibody comprising a portion encoded by a human Ig locus and a portion encoded by a rat Ig locus. Chimeric antibodies include transgenic antibodies with non-human Fc-regions or artificial Fc-regions, and human idiotypes. Such immunoglobulins can be isolated from animals of the invention that have been engineered to produce such chimeric antibodies.

By "artificial Fc-region" is meant an Fc-region encoded by an artificial constant region gene.

The term "Ig gene segment" as used herein refers to segments of DNA encoding various portions of an Ig molecule, which are present in the germline of non-human animals and humans, and which are brought together in B cells to form rearranged Ig genes. Thus, "Ig gene segments" as used herein can refer to V gene segments. D gene segments. J gene segments and C region genes, as well as portions thereof.

The term "human Ig gene segment" as used herein includes both naturally occurring sequences of a human Ig gene segment, degenerate forms of naturally occurring sequences of a human Ig gene segment, as well as synthetic sequences that encode a polypeptide sequence substantially identical to the polypeptide encoded by a naturally occurring sequence of a human Ig gene segment. By "substantially" is meant that the degree of amino acid sequence identity is at least about 85%-95%. Preferably, the degree of amino acid sequence identity is greater than 90%, more preferably greater than 95%.

Targeted Integration of Donor Polynucleotides

In one aspect, the invention provides methods for targeted integration of a donor polynucleotide in an Ig locus of a mammalian embryo. The methods involve integration of a donor polynucleotide at an integration site within a chromosome of a mammalian embryo. Preferably, the mammalian embryo is a single cell fertilized oocyte. Preferred mammals include but are not limited to rodents (e.g., rats, hamsters and guinea pigs), weasels (e.g., ferrets), rabbits, farm animals, lamas, camels, and the like.

In one embodiment, the donor polynucleotide comprises an insertion sequence, which is integrated upon integration of the donor polynucleotide. The integration of the donor polynucleotide may involve insertion without deletion or replacement of endogenous genomic sequence. Alternatively, integration may involve deletion or replacement of endogenous genomic sequence, which may include an entire Ig locus.

Integration of the donor polynucleotide generates a modified genomic DNA sequence, referred to herein as a recombinant Ig locus. A portion of endogenous genomic sequence may function together with the integrated donor polynucleotide, as a functional Ig locus. Alternatively, the integrated polynucleotide may replace the endogenous Ig locus and function on its own.

Integration of a donor polynucleotide into the chromosome is mediated by homologous recombination. The present methods comprise the use of a meganuclease to generate a single- or double-strand break to stimulate integration of the donor polynucleotide by homologous recombination. The donor polynucleotide comprises two homology arms that are nucleotide sequences homologous to genomic DNA sequences, at least one of which is proximal to the meganuclease cleavage site. In one embodiment, the donor polynucleotide comprises an insertion sequence, which is flanked by the homology arms.

A "target site" comprises a "binding site" for a meganuclease, as well as a "cleavage site" for the meganuclease, which cleavage site may be situated in or near the binding site. If the cleavage site is not in the binding site, the target site further comprises intervening sequence therebetween.

A meganuclease used in the present methods binds in a sequence-specific manner to a binding site within a desired target site at or proximal to an Ig locus in chromosomal DNA. The target site is a chromosomal nucleotide sequence that can be any nucleotide sequence situated at or proximal to a point where it is desired to integrate a donor polynucleotide in an Ig locus (the "integration site"). By "proximal to" is meant within a distance that facilitates homologous recombination at the integration site. It is known in the art that cleavage can stimulate homologous recombination at a distance (see, for example. Townsend et al., Nature, 459, 442-445, 2009). Preferably, "proximal to" refers to within 10 kb, more preferably within 2 kb, more preferably within 1.5 kb, and most preferably within 1 kb of the integration site in the Ig locus.

As an example, the target site may be situated at or proximal to a location that contains a gene segment which is to be deleted or replaced, or in which it is desired to introduce a mutation, such as a point mutation or deletion. It may be desirable to replace all or a portion of the endogenous gene segment with a donor polynucleotide. Further, it may be desirable to replace multiple gene segments, or the entire Ig locus, with one or more donor polynucleotides. A target site can be in the coding region of an Ig locus, in transcribed non-coding regions such as, for example, leader sequences, trailer sequences or introns, or in non-transcribed regions, either upstream or downstream of the coding region. A target site can also be at or proximal to a location lacking an endogenous gene segment, but within an Ig locus, wherein it is desired to insert a donor polynucleotide.

In accordance with the present teachings, a meganuclease binds to a binding site within a target site and cleaves the bound genomic DNA at a cleavage site located in or near the binding site to facilitate integration of a donor polynucleotide at or proximal to the cleavage site.

In one embodiment, a meganuclease DNA binding domain is engineered to bind a chromosomal DNA sequence at or near a predetermined cleavage site in or proximal to a desired integration site in an Ig locus and facilitate cleavage at the predetermined cleavage site.

In one embodiment, a meganuclease DNA binding domain is engineered to bind a predetermined chromosomal DNA sequence and the cleavage site is mapped experimentally.

Upon binding the binding site, a meganuclease cleaves bound chromosomal DNA at or near the binding site using its cleavage domain. The exact site of cleavage depends on the particular meganuclease used. The binding site (i.e., the meganuclease DNA binding sequence) can encompass the cleavage site, or the near edge of the binding site can be 1, 2, 3, 4, 5, 6, 10, 25, 50 or more nucleotides (or any integral value between 1 and 50 nucleotides) from the cleavage site. In one embodiment, cleavage occurs within the binding site, between two half-sites that serve as the binding site for the meganuclease.

Methods for mapping cleavage sites in vitro and in vivo are known to those of skill in the art.

The targeted integration methods of the invention involve introducing at least one meganuclease into the embryo in the presence of a donor polynucleotide. The meganuclease may be introduced before the donor polynucleotide, or vice versa, or the meganuclease and donor polynucleotide may be co-introduced at the same time. The meganuclease may be introduced into the embryo as a protein. A meganuclease may be produced and purified using conventional techniques. The purified meganuclease may then be quantified and an effective amount introduced into the embryo to enhance the frequency of homologous recombination. Alternatively, a meganuclease may be introduced into the embryo by introducing into the embryo an encoding nucleic acid that is expressed in the embryo. The encoding nucleic acid may be, for example, in the form of an encoding mRNA, or an expression vector containing a nucleotide sequence encoding the meganucelase operably linked to a promoter. In a preferred embodiment, an mRNA encoding the meganuclease is introduced into the embryo. In embodiments employing an expression construct, an inducible expression construct is especially preferred.

The meganuclease or meganuclease encoding nucleic acid may be introduced into the embryo using any desired technique known in the art. In a preferred embodiment, microinjection is used to introduce a meganuclease or meganuclease encoding nucleic acid into the embryo. Another preferred method for nucleic acid introduction is by viral means (e.g., HIV, or adenovirus).

In an especially preferred embodiment, microinjection is used to co-introduce a meganuclease encoding nucleic acid and donor polynucleotide into the pronucleus of an embryo. In another especially preferred embodiment, microinjection is used to co-introduce a meganuclease encoding nucleic acid and donor polynucleotide into the cytoplasm of an embryo.

In another embodiment, a meganuclease expression construct is present in the genome of a parent of the embryo and consequently in the genome of the embryo, and the encoded meganuclease is produced in the embryo. In a preferred embodiment, the expression construct is an inducible expression construct, and expression of the encoded meganuclease is induced in the embryo. Such constructs provide for minimization of cytotoxic effects associated with expression of a particular meganuclease through controlled expression via inducible promoters, e.g., heat-inducible promoters, radiation-inducible promoters, tetracycline operon, hormone inducible promoters, and promoters inducible by dimerization of transactivators, and the like. For example, see Vilaboa et al., Current Gene Therapy, 6:421-438, 2006. Such strains are convenient and find use for the generation of many different recombinant Ig loci through the use of different donor polynucleotides.

In one embodiment, the meganuclease is a nickase. Use of a nickase may be preferable to a meganuclease that creates double-strand breaks because of the lower toxicity of the nickase. Nickases are endodeoxynucleases having a substitution in the active site which causes these enzymes to make single strand nicks rather than double strand breaks at a cleavage site. Nickases can stimulate homologous recombination, albeit at a lower frequency than endonucleases. (Smith et al., PNAS, 106:5099-5104, 2009.)

In some embodiments, it may be desired to insert a donor polynucleotide in more than one chromosomal site. The target sites may have the same sequence, or may have different sequences. If the target sites have different sequences, more than one meganuclease is used. In one embodiment, multiple homologous recombination events are facilitated in an embryo to introduce donor polynucleotides into the chromosomal loci. Alternatively, one or both parents from which the embryo is derived may comprise a donor polynucleotide inserted at an integration site, and insertion of the donor polynucleotide at an additional integration site may be done in the embryo using the methods disclosed herein. Multiple homologous recombination events may also be done with multiple different donor polynucleotides.

Multiple integration sites may be within the same or different Ig loci, and different loci can include the maternal and paternal alleles of the same Ig gene complex. For example, multiple genes in one Ig locus may be targeted by meganucleases and donor polynucleotides for homologous recombination. As well, the same or different gene segments in different Ig loci may be targeted by meganucleases and donor polynucleotides.

In one embodiment, a cleavage site in close proximity (e.g., within 2 kb) to or in an Ig locus is selected in order to facilitate replacement of the entire Ig locus or parts thereof with an artificial Ig locus by homologous recombination.

In some embodiments, the donor polynucleotide or a portion thereof may be located between two sites that facilitate excision or rearrangement, e.g., lox P sites and flp sites. When the donor polynucleotide or a portion thereof is located between lox P sites, the inserted sequence or portion thereof may be removed from the genome of the cell by providing the Cre protein. Ore may be provided in the cells in which a homologous recombination event has occurred by introducing Cre or a CRE-encoding nucleic acid, or inducing Cre expression, using any method available in the art. When the donor polynucleotide or a portion thereof is located between flp sites, the inserted sequence or portion thereof may be removed from the genome of the cell by providing the flp recombinase, flp-recombinase may be provided in the cells in which a homologous recombination event has occurred by introducing flp-recombinase or a flp-recombinase-encoding nucleic acid, or inducing flp-recombinase expression, using any method available in the art In one embodiment, the donor polynucleotide comprises a nucleotide sequence which encodes a detectable or selectable marker which facilitates the identification or selection of cells or organisms in which the desired homologous recombination event has occurred, For example, the detectable marker may be a detectable tag.

If desired, the chromosomal structure of cells of the resultant mammal produced by the methods herein may be verified using techniques such as PCR or Southern blotting.

The donor polynucleotide may be introduced into the embryo concurrently with the meganuclease, prior to the meganuclease, or after the meganuclease. Following cleavage at a cleavage site by a meganuclease, a donor polynucleotide is integrated into the chromosome at or proximal to the cleavage site by homologous recombination. The donor polynucleotide contains sufficient homology to the genomic sequence at or proximal to the cleavage site to facilitate homologous recombination.

Depending on the homologous recombination mechanism, the donor polynucleotide molecule per se may not be incorporated into the chromosomal integration site (e.g., homologous recombination by synthesis dependent strand annealing—see for example, Moehle et al., PNAS, 104:3055-3060, 2007). For example, a donor polynucleotide may be copied and the copy may be inserted into the chromosomal integration site.

Donor Polynucleotides

A "donor polynucleotide" refers to a polynucleotide that is capable of being integrated, in whole or in part, into the Ig locus of a mammalian genome by homologous recombination in accordance with the present methods. In one embodiment, a "donor polynucleotide" comprises an "insertion sequence", which is capable of being integrated into the Ig locus of a mammalian genome by homologous recombination. An insertion sequence can be of any length that homologous recombination will accommodate, and may encompass an entire artificial Ig locus.

A donor polynucleotide once inserted into a chromosome is sometimes referred to herein as an "inserted polynucleotide" or "inserted sequence".

Insertion sequences, alone or in combination with one or more homology arms or portions thereof, preferably comprise at least one Ig gene segment, or portion thereof. In one embodiment, the insertion sequence is a gene sequence from the same species as the subject embryo. Alternatively, the gene sequence may be from a species other than that of the subject embryo. In a preferred embodiment, an insertion sequence is a human Ig gene segment or portion thereof. In a preferred embodiment, a donor polynucleotide comprises a plurality of human Ig gene segments, with a plurality of human V gene segments being especially preferred.

In one embodiment, a donor polynucleotide comprises an insertion sequence comprising a V gene segment or portion thereof. In a preferred embodiment, the V gene segment is a human V gene segment, or portion thereof. In one embodiment, the V gene segment is a light chain V gene segment, or portion thereof. In one embodiment, the V gene segment is a heavy chain V gene segment, or portion thereof.

In one embodiment, a donor polynucleotide comprises an insertion sequence comprising a J gene segment, or portion thereof. In a preferred embodiment, the J gene segment is a human J gene segment, or portion thereof. In one embodiment, the J gene segment is a heavy chain J gene segment, or portion thereof. In one embodiment, the J gene segment is a light chain J gene segment, or portion thereof.

In one embodiment, a donor polynucleotide comprises an insertion sequence comprising a D gene segment, or portion thereof. In a preferred embodiment, the D gene segment is a human D gene segment, or portion thereof.

Naturally occurring Ig gene segment sequences, degenerate forms thereof, and synthetic nucleotide sequences encoding polypeptides with substantial identity to those encoded by naturally occurring Ig gene segments are included.

In one embodiment, an insertion sequence comprises a human C gene or portion thereof, with human CH1 domain encoding exons being especially preferred.

Homologous recombination may also be used to knock out endogenous C genes, including endogenous C gene exons encoding CH1 domains.

In one embodiment, an insertion sequence comprises an artificial Ig locus, as described herein.

In one embodiment, the insertion sequence comprises an Ig gene segment or portion thereof and may be used to replace an endogenous gene segment. For example, a donor polynucleotide comprising a human $V_H$ gene segment may replace an endogenous $V_H$ gene segment in the Ig heavy chain locus of a non-human genome.

In some embodiments, the insertion sequence introduces one or more mutations into an endogenous chromosomal gene upon homologous recombination. The mutation(s) may disrupt the endogenous chromosomal gene or, alternatively, may enhance, restore, or otherwise modify its activity.

In some embodiments, the insertion sequence inhibits production of an endogenous gene product following integration by homologous recombination. For example, an insertion sequence may introduce a deletion into an endogenous gene or may introduce a stop codon therein. A insertion sequence may comprise a non-functional sequence that is used to replace a functional genomic sequence. In such embodiments, the integrated sequence may "knock out" or functionally ablate the target gene.

In one embodiment, the insertion sequence is an artificial Ig locus and replaces an endogenous Ig locus.

In some embodiments, it may be desirable to inactivate an endogenous locus, for example, as detailed in U.S.S.N. 12/130,818 filed 30 May 2008. Meganucleases may be used to inactivate an endogenous locus, as described in U.S. Ser. No. 12/130,818. Additionally, donor polynucleotides comprising an insertion sequence or lacking an insertion sequence may be used with a meganuclease to inactivate an endogenous locus, as described herein. For example, a donor polynucleotide that lacks an insertion sequence may be used to delete the genomic sequence between those genomic sequences homologous to the homology arms of the donor polynucleotide.

The donor polynucleotide is preferably DNA, and can be single- or double-stranded, with double-stranded being preferred, and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) Proc. Natl. Acad. Sci. USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A donor polynucleotide can be introduced into an embryo using any method known in the art, including but not limited to the use of calcium phosphate transfection, polybrene, protoplast fusion, electroporation, ultrasonic methods (e.g., sonoporation), liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra).

A preferred method of introduction is microinjection. Another preferred method for introduction is by viral means (e.g., HIV, or adenovirus).

Sequences in a donor polynucleotide may be subject to codon optimization to allow for optimal expression, where the donor nucleotide codons found in one species may be altered at the nucleic acid level to the nucleotide codons preferred in the recipient genome.

A donor polynucleotide comprises homology arms, which are a 5'-end sequence and a 3'-end sequence, which 5'- and 3'-end sequences are homologous to genomic DNA sequences, at least one of which is in close proximity to the cleavage site. The 5'- and 3'-end sequences need not run to the termini of the donor polynucleotide. The 5'-end and 3'-end sequences facilitate homologous recombination following cleavage of the chromosome by a meganuclease, and thereby provide for integration of the donor polynucleotide. In one embodiment, the donor polynucleotide comprises an insertion sequence flanked by the homology arms. The 5'- and/or 3'-end sequences or portions thereof are integrated, along with the insertion sequence, if present, by homologous recombination. The homology arms may function together with the insertion sequence (e.g., by forming part of the Ig gene segment of the insertion sequence).

The degree of sequence identity between the 5'- and 3'-end sequences and chromosomal sequences is sufficient to facilitate homologous recombination by normal cellular mechanisms in a mammalian embryo following cleavage at the cleavage site by a meganuclease. The lengths of the 5'- and 3'-end sequences may be any lengths which permit homologous recombination to occur. For example, the 5'- and 3'-end sequences can range in length from 10 to 5,000 nucleotides (or any integral value of nucleotides therebetween) or longer. In general, the longer the 5'- and 3'-end sequences, the higher the efficiency of homologous recombination. Generally, the 5'- and 3'-end sequences will have at least 50%, more preferably 60%, 70%, 80%, 90%, 95%, 98%, 99%, or 100% sequence identity to genomic sequences.

An "homologous" sequence generally refers to a nucleotide sequence that shares a degree of sequence identity with a second nucleotide sequence. In the present invention, 5'-end sequences and 3'-end sequences of a donor polynucleotide are homologous to chromosomal DNA sequences. The degree of sequence identity between the 5'"- and 3'-end sequences and chromosomal sequences is sufficient to facilitate homologous recombination by normal cellular mechanisms in a mammalian embryo following cleavage by a meganuclease.

An insertion sequence or portion thereof may be homologous to a chromosomal nucleotide sequence at an integration site (e.g., for correction of a genomic point mutation, or replacement of a related exon or gene segment, by targeted homologous recombination). In alternative embodiments, an insertion sequence is not homologous to a chromosomal nucleotide sequence at the integration site. In the latter embodiments, the corresponding donor polynucleotide nevertheless comprises sequences homologous to chromosomal sequences in the form of the included 5'- and 3'-end sequences described herein.

Techniques for determining nucleic acid sequence identity are known in the art. Typically, such techniques include determining the nucleotide sequence of a first polynucleotide and comparing the sequence to that of a second polynucleotide. In general, identity refers to an exact nucleotide-to-nucleotide correspondence. The percent identity of two sequences is the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). See also the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects sequence identity. Other suitable programs for calculating the percent identity or similarity between sequences are generally known in the art, for example, another alignment program is BLAST, which may be used with default parameters.

Alternatively, the degree of sequence similarity between polynucleotides can be determined by hybridization using techniques well known in the art. Substantially homologous polynucleotide sequences useful for homologous recombination can be identified in, for example, a Southern hybridization experiment under, for example, stringent conditions, as defined for that particular system. Defining appropriate hybridization conditions is within the skill of the art. See, e.g., Sambrook et al., supra; Nucleic Acid Hybridization: A Practical Approach, editors B. D. Hames and S. J. Higgins, (1985) Oxford; Washington, D.C.; IRL Press). Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations. The selection of a particular set of hybridization conditions is selected following standard methods in the art (see, for example, Sambrook, et al., Molecular Cloning: A Laboratory Manual, Second Edition, (1989) Cold Spring Harbor, N.Y.).

Meganucleases

By "meganuclease" is meant an endodeoxyribonuclease that recognizes long recognition sites in DNA, preferably at least 12, more preferably at least 13, more preferably at least 14, more preferably at least 15, more preferably at least 16, more preferably at least 17, and most preferably at least 18 nucleotides in length. Meganucleases include zinc-finger nucleases, naturally occurring homing endonucleases and custom engineered zinc-finger nucleases and homing endonucleases. For more discussion of meganucleases, see, for example, U.S. Patent Application Publication Nos. 20060206949, 20060153826, 20040002092, 20060078552, and 20050064474.

As used in the present disclosure, "meganuclease" also embraces variant meganucleases, often referred to in the art as "nickases". Nickases are endodeoxynucleases having a substitution in the active site which causes these enzymes to make single strand nicks rather than double strand breaks at a cleavage site. Nickases can stimulate homologous recombination, albeit at a lower frequency than endonucleases. (Smith et al., PNAS, 106:5099-5104, 2009.)

Accordingly, as used herein, "meganuclease" includes enzymes that can generate a breakage of one or both covalent backbones of a double-stranded DNA molecule. Single-strand breaks are sometimes referred to herein as "nicks".

Zinc-finger nucleases with altered specificity can be generated by combining individual zinc fingers with different triplet targets. The specificity of naturally occurring homing endonucleases can be altered by structure-based protein engineering. For example, see Proteus and Carroll, Nature Biotechnology 23(8):967-97, 2005. See also Remy et al., Zinc-finger nucleases: a powerful tool for genetic engineering of animals, Transgenic Res. 2009 Sep. 26 epub ahead of print.

Meganucleases can be engineered to bind to a predetermined nucleotide sequence using any of the methods known in the art. Methods for engineering meganucleases may include rational design and/or selection. A rationally designed meganuclease is a protein not occurring in nature and the composition of which results principally from rational criteria. Rational criteria for design include application of substitution rules and computerized algorithms for processing information in a database storing information of existing meganuclease designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A selected meganuclease is a protein not found in nature whose production results primarily from an empirical process such as phage display, interaction trap or hybrid selection. See e.g., U.S. Pat. No. 5,789,538: U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084.

Expression Vectors

A nucleic acid encoding one or more meganucleases can be cloned into an expression vector for use in the invention.

An expression vector contains a promoter to direct transcription of an operably linked nucleic acid. Suitable bacterial and eukaryotic promoters are well known in the art and described, e.g., in Sambrook et al., Molecular Cloning, A Laboratory Manual (2nd ed. 1989; 3$^{rd}$ ed., 2001); Kriegler, Gene Transfer and Expression: A Laboratory Manual (1990); and Current Protocols in Molecular Biology (Ausubel et al., supra). Eukaryotic expression systems for mammalian cells are well known by those of skill in the art and are commercially available.

In addition to the promoter, the expression vector typically contains a transcription unit or expression cassette that contains all the additional elements required for the expression of the nucleic acid in host cells. A typical expression cassette thus contains a promoter operably linked, e.g., to a nucleic acid sequence encoding a therapeutic protein, and signals required, e.g., for efficient polyadenylation of the transcript, transcriptional termination, ribosome binding sites, or translation termination. Additional elements of the cassette may include, e.g., enhancers, and heterologous splicing signals.

Transcriptional regulatory elements, such as promoters and enhancers and combinations thereof, are sometimes referred to herein as "regulatory elements, "regulatory sequences, or "expression control regions".

Any of the well known procedures for introducing foreign nucleotide sequences into host cells may be used. These include the use of calcium phosphate transfection, polybrene, protoplast fusion, electroporation, ultrasonic methods (e.g., sonoporation), liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). Microinjection into the embryo is particularly preferred. Introduction of nucleic acids by viral means (e.g. HIV, or adenovirus) is also preferred.

The terms "operative linkage", "operatively linked", and "operably linked" are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operably linked to a coding sequence if the transcriptional regulatory sequence controls the level of transcription of the coding sequence in response to the presence or absence of one or more transcriptional regulatory factors. A transcriptional regulatory sequence is generally operably linked in cis with a coding sequence, but need not be directly adjacent to it. For example, an enhancer is a transcriptional regulatory sequence that is operably linked to a coding sequence, even though they are not contiguous.

Enhancement of Homologous Recombination

Any of the following approaches may be used alone or in combination to enhance homologous recombination.

To enhance homologous recombination, the expression of genes involved in homologous recombination, such as, for example, members of the RAD52 epistasis group (e.g., Rad50, Rad51, Rad51B, Rad51C, Rad51D, Rad52, Rad54, Rad54B, Mre11, XRCC2, XRCC3), genes whose products interact with the aforementioned gene products (e.g., BRCA1, BRCA2) and/or genes in the NBS1 complex, may be appropriately modulated. Similarly, the expression of genes involved in non-homologous end joining (e.g., Ku70/80, XRCC4, poly(ADP ribose) polymerase. DNA ligase 4) may be inhibited. See, for example, Yanez et al. (1998) Gene Therapy 5:149-159; Hoeijmakers (2001) Nature 411:366-374; Johnson et al. (2001) Biochem. Soc. Trans. 29:196-201; Tauchi et al. (2002) Oncogene 21:8967-8980. Methods for activation and repression of gene expression using fusions between a zinc finger binding domain and a functional domain are disclosed, for example, in U.S. Pat. Nos. 6,534,261; 6,824,978 and 6,933,113. Additional repression methods include the use of antisense oligonucleotides and/or small interfering RNA (siRNA or RNAi) targeted to the sequence of the gene to be repressed.

The p53 protein has been reported to play a central role in repressing homologous recombination. See, for example, Valerie et al., (2003) Oncogene 22:5792-5812; Janz, et al. (2002) Oncogene 21:5929-5933. For example, the rate of homologous recombination in p53-deficient human tumor lines is 10.000-fold greater than in primary human fibroblasts, and there is a 100-fold increase in homologous recombination in tumor cells with a non-functional p53 compared to those with functional p53. Mekeel et al. (1997) Oncogene 14:1847-1857. In addition, overexpression of p53 dominant negative mutants leads to a 20-fold increase in spontaneous recombination. Bertrand et al. (1997) Oncogene 14:1117-1122. Analysis of different p53 mutations has revealed that the roles of p53 in transcriptional transactivation and G1 cell cycle checkpoint control are separable from its involvement in homologous recombination. Saintigny et al. (1999) Oncogene 18:3553-3563; Boehden et al. (2003) Oncogene 22:4111-4117. Accordingly, downregulation of p53 activity can serve to increase the efficiency of targeted homologous recombination. Any method for downregulation of p53 activity can be used, including but not limited to antisense, siRNA, expression of a p53 dominant negative mutant or targeted repression of p53 gene expression according to methods disclosed, e.g., in U.S. Pat. No. 6,534,261.

Increases in efficiency of targeted homologous recombination may be achieved by blocking the cells in the $G_2$ phase of the cell cycle, when homology-driven repair processes are maximally active. Such arrest can be achieved in a number of ways. For example, cells can be treated with e.g., drugs, compounds and/or small molecules which influence cell-cycle progression so as to arrest cells in $G_2$ phase. Exemplary molecules of this type include, but are not limited to, compounds which affect microtubule polymerization (e.g., vinblastine, nocodazole. Taxol), compounds that interact with DNA (e.g., cis-platinum(II) diamine dichloride. Cisplatin, doxorubicin) and/or compounds that affect DNA synthesis (e.g., thymidine, hydroxyurea. L-mimosine, etoposide, 5-fluorouracil).

Increases in recombination efficiency may be achieved by the use of histone deacetylase (HDAC) inhibitors (e.g., sodium butyrate, trichostatin A) which alter chromatin structure to make genomic DNA more accessible to meganucleases and the cellular recombination machinery.

Additional methods for cell-cycle arrest and homologous recombination enhancement include overexpression of proteins which inhibit the activity of the CDK cell-cycle kinases, for example, by introducing a cDNA encoding the protein into the cell or by inducing expression of the endogenous gene encoding the protein. Cell-cycle arrest is also achieved by inhibiting the activity of cyclins and CDKs, for example, using RNAi methods (e.g., U.S. Pat. No. 6,506,559) or other methods. See, e.g., U.S. Pat. No. 6,534,261 for methods for the synthesis of engineered zinc finger proteins for regulation of gene expression.

In addition, methods of screening for cellular factors that facilitate homologous recombination are known and may be employed in the present invention. See, for example, U.S. 20070134796 and citations therein.

Transgenic Animals Comprising a Recombinant Ig Locus

In one aspect, the invention provides transgenic animals comprising a recombinant Ig locus. The transgenic animals are mammals. Preferred mammals include but are not limited to rodents (e.g., rats, hamsters and guinea pigs), weasels (e.g., ferrets), rabbits, farm animals, lamas and camels, and the like The transgenic animals include primary animals obtained directly from embryos manipulated in accordance with the invention, as well as animals derived from such primary animals and/or manipulated embryos. The transgenic animals carry at least one recombinant Ig locus, which is preferably functional and capable of producing a repertoire of immunoglobulin molecules, including transgenic immunogloblins, in the transgenic animal.

In a preferred embodiment, the transgenic animals comprise a recombinant Ig heavy chain locus and a recombinant Ig light chain locus that are each functional and capable of producing a repertoire of immunoglobulin molecules, including transgenic immunoglobulins, in the transgenic animal.

In a preferred embodiment, the transgenic animals are capable of producing antibodies having a human idiotype. In one embodiment, transgenic animals comprise a recombinant Ig locus including a non-human C gene, and are capable of producing chimeric antibodies having a human idiotype and non-human constant region. In one embodiment, transgenic animals comprise a recombinant Ig locus including a human C gene and are capable of producing antibodies having a human idiotype and a human constant region.

In one embodiment, the transgenic animals comprise a recombinant Ig heavy chain locus, and lack a functional Ig light chain locus. Such animals find use in the production of heavy chain-only antibodies. The inactivation of an endogenous Ig light chain locus may be done using a meganuclease, as disclosed in U.S. Ser. No. 12/130,818 filed 30 May 2008. Inactivation of an endogenous locus may also be done using meganuclease cleavage-stimulated homologous recombination, as described herein.

Production of the transgenic animals involves the integration of a donor polynucleotide in an Ig locus. The methods may involve integration at more than one Ig locus. The methods may involve integration of more than one donor polynucleotide at more than one site in the same Ig locus or in different Ig loci. The methods may involve replacement of endogenous Ig gene segments with donor polynucleotides comprising exogenous Ig gene segments. The methods may also involve replacement of an endogenous Ig locus with an artificial Ig locus.

The recombinant Ig loci generated by the subject methods may include multiple Ig gene segments that comprise donor polynucleotides or portions thereof. These gene segments may include V gene segments, J gene segments, D gene segments in the case of a heavy chain locus, and constant region genes.

In a preferred embodiment, a recombinant Ig locus comprises an integrated donor polynucleotide comprising a human Ig gene segment or portion thereof. In a preferred embodiment, a recombinant Ig locus comprises a plurality of human Ig gene segments, with a plurality of human V gene segments being especially preferred, which is produced by integration of one or more donor polynucleotides.

In one embodiment, a recombinant Ig locus comprises an integrated donor polynucleotide comprising a V gene segment, or portion thereof. In a preferred embodiment, the V gene segment is a human V gene segment, or portion thereof. In one embodiment, the V gene segment is a light chain V gene segment, or portion thereof. In one embodiment, the V gene segment is a heavy chain V gene segment, or portion thereof.

In one embodiment, a recombinant Ig locus comprises an integrated donor polynucleotide comprising a J gene segment, or portion thereof. In a preferred embodiment, the J gene segment is a human J gene segment, or portion thereof. In one embodiment, the J gene segment is a heavy chain J gene segment, or portion thereof. In one embodiment, the J gene segment is a light chain J gene segment, or portion thereof.

In one embodiment, a recombinant Ig locus comprises an integrated donor polynucleotide comprising a D gene segment, or portion thereof. In a preferred embodiment, the D gene segment is a human D gene segment, or portion thereof.

Naturally occurring Ig gene segment sequences, degenerate forms thereof, and synthetic nucleotide sequences encoding polypeptides with substantial identity to those encoded by naturally occurring Ig gene segments are included.

In one embodiment, a recombinant Ig locus comprises an integrated donor polynucleotide comprising a non-human C region gene, or a portion thereof. Such transgenic animals have the capacity to produce a diversified repertoire of immunoglobulin molecules, which include immunoglobulins having a non-human constant region.

In one embodiment, a recombinant Ig locus comprises an integrated donor polynucleotide that comprises a human C region gene. Such transgenic animals have the capacity to produce a diversified repertoire of immunoglobulin molecules, which include immunoglobulins having a human constant region.

In one embodiment, a recombinant Ig locus comprises an integrated donor polynucleotide comprising an artificial constant region gene. For example, an exemplary artificial C constant region gene is a constant region gene encoding a human IgG $C_{H1}$ domain and rat IgG $C_{H2}$ and $C_{H3}$ domain. Such transgenic animals have the capacity to produce a diversified repertoire of immunoglobulin molecules, which include antibodies having an artificial constant region comprising both human and non-human components.

Transgenic animals having combinations of integrated donor polynucleotides at a plurality of sites in a recombinant Ig locus are also provided. For example, a recombinant Ig locus that comprises an integrated donor polynucleotide comprising a human C region gene, and an integrated donor polynucleotide comprising a human V gene segment are contemplated.

In one embodiment, a recombinant Ig locus comprises an artificial Ig locus as described herein.

In a preferred embodiment, transgenic animals of the invention have the capacity to produce a diversified repertoire of antibodies, including transgenic antibodies having a human idioptype.

Recombinant Immunoglobulin Loci

Each recombinant Ig locus comprises multiple immunoglobulin gene segments, which include at least one V gene segment, one or more J gene segments, one or more D gene segments in the case of a heavy chain locus, and one or more constant region genes.

In a preferred embodiment, a recombinant Ig locus comprises an integrated donor polynucleotide comprising a human Ig gene segment or portion thereof. In a preferred embodiment, a recombinant Ig locus comprises a plurality of human Ig gene segments, with a plurality of human V gene segments being especially preferred, which is produced by the integration of one or more donor polynucleotides.

In one embodiment, a recombinant Ig locus comprises an integrated donor polynucleotide comprising a V gene segment, or portion thereof. In a preferred embodiment, the V gene segment is a human V gene segment, or portion thereof. In one embodiment, the V gene segment is a light chain V gene segment, or portion thereof. In one embodiment, the V gene segment is a heavy chain V gene segment, or portion thereof.

In one embodiment, a recombinant Ig locus comprises an integrated donor polynucleotide comprising a J gene segment, or portion thereof. In a preferred embodiment, the J gene segment is a human J gene segment, or portion thereof. In one embodiment, the J gene segment is a heavy chain J gene segment, or portion thereof. In one embodiment, the J gene segment is a light chain J gene segment, or portion thereof.

In one embodiment, a recombinant Ig locus comprises an integrated donor polynucleotide comprising a D gene segment, or portion thereof. In a preferred embodiment, the D gene segment is a human D gene segment, or portion thereof.

Naturally occurring Ig gene segment sequences, degenerate forms thereof, and synthetic nucleotide sequences encoding polypeptides with substantial identity to those encoded by naturally occurring Ig gene segments are included.

In one embodiment, a recombinant Ig locus comprises at least one or several rat constant region genes, e.g., C$\Delta$, C$\mu$, and C$\gamma$ (including any of the C$\gamma$ subclasses).

In one embodiment, a recombinant light chain Ig locus comprises a C-region having at least one rat C gene (e.g., rat C$\lambda$ or C$\kappa$).

Artificial Ig Loci

The present invention is further directed to artificial Ig loci and their use as insertion sequences in making transgenic animals capable of producing immunoglobulins having a human idiotype.

An artificial Ig locus comprises multiple immunoglobulin gene segments, which include at least one V gene segment, one or more J gene segments, one or more D gene segments in the case of a heavy chain locus, and one or more constant region genes. In the present invention, at least one of the V gene segments is a human V gene segment. Preferably the artificial loci comprises a plurality of human V gene segments. In heavy chain loci human or non-human-derived D gene segments may be included in the artificial Ig loci. In a preferred embodiment, an artificial Ig locus comprises a human D gene segment. In a preferred embodiment, an artificial Ig locus comprises a human J gene segment. The gene segments in such loci are juxtaposed with respect to each other in an unrearranged configuration (or "the germline configuration"), or in a partially or fully rearranged configuration. The artificial Ig loci have the capacity to undergo gene rearrangement (if the gene segments are not fully rearranged) in the subject animal thereby producing a diversified repertoire of immunoglobulins having human idiotypes.

Regulatory elements like promoters, enhancers, switch regions, recombination signals, and the like may be of human or non-human origin. What is required is that the elements be operable in the animal species concerned, in order to render the artificial loci functional.

In one aspect, the invention provides transgenic constructs containing an artificial heavy chain locus capable of undergoing gene rearrangement once integrated in the host animal genome and thereby producing a diversified repertoire of heavy chains having human idiotypes. An artificial heavy chain locus of the transgene contains at least one human V gene segment. Preferably, the V-region includes at least about 5-100 human heavy chain V (or "$V_H$") gene segments. A human $V_H$ segment encompasses naturally occurring sequences of a human $V_H$ gene segment, degenerate forms of naturally occurring sequences of a human $V_H$ gene segment, as well as synthetic sequences that encode a polypeptide sequence substantially identical to that encoded by a naturally occurring human V gene segment.

In a preferred embodiment, the artificial heavy chain locus contains at least one or several animal derived constant region genes, e.g., C$\Delta$, C$\mu$ and C$\gamma$ (including any of the C$\gamma$ subclasses).

In one embodiment, the artificial heavy chain Ig locus may comprise C genes from different species, preferably human.

In one embodiment, the artificial heavy chain locus contains artificial constant region genes. In a preferred embodiment, such artificial constant region genes encode a human $C_{H1}$ domain and non-human $C_{H2}C_{H3}$ domains, or a human $C_{H1}$ and non-human derived $C_{H2}$, $C_{H3}$ and $C_{H4}$ domains. A hybrid heavy chain with a human $C_{H1}$ domain pairs effectively with a fully human light chain.

In one embodiment, the artificial heavy chain locus contains artificial constant region genes lacking $C_{H1}$ domains. In a preferred embodiment, such artificial constant region genes encode truncated IgM and/or IgG lacking the $C_{H1}$ domain but comprising $C_{H2}$, and $C_{H3}$, or $C_{H2}$, $C_{H3}$ and $C_{H4}$ domains. Heavy chains lacking $C_{H1}$ domains cannot pair effectively with Ig light chains and form heavy chain only antibodies.

In another aspect, the invention provides transgenic constructs containing an artificial light chain locus capable of undergoing gene rearrangement in the host animal thereby producing a diversified repertoire of light chains having human idiotypes. An artificial light chain locus of the transgene contains at least one human V gene segment. Preferably, the artificial light chain locus includes at least about 5-100 human light chain V (or "$V_L$") gene segments. A human $V_L$ segment encompasses naturally occurring sequences of a human $V_L$ gene segment, degenerate forms of naturally occurring sequences of a human $V_L$ gene segment, as well as synthetic sequences that encode a polypeptide sequence substantially identical to that encoded by a naturally occurring human light chain V gene segment.

In one embodiment, the artificial light chain Ig locus has a C-region having at least one animal derived C gene (e.g., animal derived C$\lambda$ or C$\kappa$).

In one embodiment, the artificial light chain Ig locus comprises a C gene from a different species, preferably human.

Another aspect of the present invention is directed to methods of making a transgenic vector containing an artificial Ig locus. Any methods available in the art may be used, and the following methods are merely exemplary.

Such methods may involve isolating Ig loci or fragments thereof, and combining the same, with one or several DNA fragments comprising sequences encoding human V region elements. The Ig gene segment(s) are inserted into the artificial Ig locus or a portion thereof by ligation or homologous recombination in such a way as to retain the capacity of the locus to undergo effective gene rearrangement in the subject animal.

Preferably, an Ig locus is isolated by screening a library of plasmids, cosmids, YACs or BACs, and the like, prepared from the genomic DNA of the same. YAC clones can carry DNA fragments of up to 2 megabases, thus an entire animal heavy chain locus or a large portion thereof can be isolated in one YAC clone, or reconstructed to be contained in one YAC clone. BAC clones are capable of carrying DNA fragments of smaller sizes (about 50-500 kb). However, multiple BAC clones containing overlapping fragments of an Ig locus can be separately altered and subsequently injected together into an animal recipient cell, wherein the overlapping fragments recombine in the recipient animal cell to generate a continuous Ig locus.

Human Ig gene segments can be integrated into the Ig locus on a vector (e.g., a BAC clone) by a variety of methods, including ligation of DNA fragments, or insertion of DNA fragments by homologous recombination. Integration of the human Ig gene segments is done preferably in such a way that the human Ig gene segment is operably linked to the host animal sequence in the transgene to produce a functional humanized Ig locus, e.g., an Ig locus capable of gene rearrangement which lead to the production of a diversified repertoire of antibodies with human idiotypes. Homologous recombination can be performed in bacteria, yeast and other cells with a high frequency of homologous recombination events. Engineered YACs and BACs can be readily isolated from the cells and used in making transgenic animals.

Immunoglobulins

Once a transgenic animal capable of producing immunoglobulins from a recombinant Ig locus is made, immunoglobulins and antibody preparations against an antigen can be readily obtained by immunizing the animal with the antigen. "Polyclonal antisera composition" as used herein includes affinity purified polyclonal antibody preparations.

In a preferred embodiment, the transgenic animal is capable of producing antibodies having a human idiotype.

A variety of antigens can be used to immunize a transgenic animal. Such antigens include but are not limited to, microorganisms, e.g. viruses and unicellular organisms (such as bacteria and fungi), alive, attenuated or dead, fragments of the microorganisms, or antigenic molecules isolated from the microorganisms.

Preferred bacterial antigens for use in immunizing an animal include purified antigens from Staphylococcus aureus such as capsular polysaccharides type 5 and 8, recombinant versions of virulence factors such as alpha-toxin, adhesin binding proteins, collagen binding proteins, and fibronectin binding proteins. Preferred bacterial antigens also include an attenuated version of *S. aureus, Pseudomonas aeruginosa, enterococcus, enterobacter*, and *Klebsiella pneumoniae*, or culture supernatant from these bacteria cells. Other bacterial antigens which can be used in immunization include purified lipopolysaccharide (LPS), capsular antigens, capsular polysaccharides and/or recombinant versions of the outer membrane proteins, fibronectin binding proteins, endotoxin, and exotoxin from *Pseudomonas aeruginosa, enterococcus, enterobacter*, and *Klebsiella pneumoniae*.

Preferred antigens for the generation of antibodies against fungi include attenuated version of fungi or outer membrane proteins thereof, which fungi include, but are not limited to, *Candida albicans, Candida parapsilosis, Candida tropicalis*, and *Cryptococcus neoformans*.

Preferred antigens for use in immunization in order to generate antibodies against viruses include the envelop proteins and attenuated versions of viruses which include, but are not limited to respiratory synctial virus (RSV) (particularly the F-Protein), Hepatitis C virus (HCV), Hepatitis B virus (HBV), cytomegalovirus (CMV), EBV, and HSV.

Antibodies specific for cancer can be generated by immunizing transgenic animals with isolated tumor cells or tumor cell lines as well as tumor-associated antigens which include, but are not limited to, Her-2-neu antigen (antibodies against which are useful for the treatment of breast cancer); CD20, CD22 and CD53 antigens (antibodies against which are useful for the treatment of B cell lymphomas), prostate specific membrane antigen (PMSA) (antibodies against which are useful for the treatment of prostate cancer), and 17-1A molecule (antibodies against which are useful for the treatment of colon cancer).

The antigens can be administered to a transgenic animal in any convenient manner, with or without an adjuvant, and can be administered in accordance with a predetermined schedule.

Routine methods well known in the art may be used to make monoclonal antibodies. For example, spleen cells may be isolated from the immunized transgenic animal and used either in cell fusion with transformed cell lines for the production of hybridomas, or cDNAs encoding antibodies may be cloned by standard molecular biology techniques and expressed in transfected cells. The procedures for making monoclonal antibodies are well established in the art. See, e.g., European Patent Application 0 583 980 A1 ("Method For Generating Monoclonal Antibodies From Rabbits"), U.S. Pat. No. 4,977,081 ("Stable Rabbit-Mouse Hybridomas And Secretion Products Thereof"), WO 97/16537 ("Stable Chicken B-cell Line And Method of Use Thereof"), and EP 0 491 057 B1 ("Hybridoma Which Produces Avian Specific Immunoglobulin G"), the disclosures of which are incorporated herein by reference. In vitro production of monoclonal antibodies from cloned cDNA molecules has been described by Andris-Widhopf et al., "Methods for the generation of chicken monoclonal antibody fragments by phage display". J Immunol Methods 242:159 (2000), and by Burton, D. R., "Phage display", Immunotechnology 1:87 (1995).

Chimeric monoclonal antibodies encoded by recombinant Ig loci, e.g., a rat antibody having a human idiotype, can be easily converted into fully human antibodies using standard molecular biology techniques. Fully human monoclonal antibodies are not immunogenic in humans and are appropriate for use in the therapeutic treatment of human subjects.

Heavy Chain-Only Antibodies

In one embodiment, transgenic animals which lack a functional Ig light chain locus, and comprising a recombinant heavy chain locus, are immunized with antigen to produce heavy chain-only antibodies that specifically bind to antigen.

In one embodiment, the invention provides monoclonal antibody producing cells derived from such animals, as well as nucleic acids derived therefrom. Also provided are hybridomas derived therefrom. Also provided are fully human heavy chain-only antibodies, as well as encoding nucleic acids, derived therefrom.

Teachings on heavy chain-only antibodies are found in the art. For example, see PCT publications WO02085944, WO02085945, WO2006008548, and WO2007096779. See also U.S. Pat. No. 5,840,526; U.S. Pat. No. 5,874,541; U.S. Pat. No. 6,005,079; U.S. Pat. No. 6,765,087; U.S. Pat. No. 5,800,988; EP 1589107; WO 9734103; and U.S. Pat. No. 6,015,695.

Pharmaceutical Compositions

In a further embodiment of the present invention, purified monoclonal or polyclonal antibodies are admixed with an appropriate pharmaceutical carrier suitable for administration to patients, to provide pharmaceutical compositions.

Patients treated with the pharmaceutical compositions of the invention are preferably mammals, more preferably humans, though veterinary uses are also contemplated.

Pharmaceutically acceptable carriers which can be employed in the present pharmaceutical compositions can be any and all solvents, dispersion media, isotonic agents and the like. Except insofar as any conventional media, agent, diluent or carrier is detrimental to the recipient or to the therapeutic effectiveness of the antibodies contained therein, its use in the pharmaceutical compositions of the present invention is appropriate.

The carrier can be liquid, semi-solid, e.g. pastes, or solid carriers. Examples of carriers include oils, water, saline solutions, alcohol, sugar, gel, lipids, liposomes, resins, porous matrices, binders, fillers, coatings, preservatives and the like, or combinations thereof.

Methods of Treatment

In a further aspect of the present invention, methods are provided for treating a disease in a vertebrate, preferably a mammal, preferably a primate, with human subjects being an especially preferred embodiment, by administering a purified antibody composition of the invention desirable for treating such disease.

The antibody compositions can be used to bind and neutralize or modulate an antigenic entity in human body tissues that causes or contributes to disease or that elicits undesired or abnormal immune responses. An "antigenic entity" is herein defined to encompass any soluble or cell surface bound molecules including proteins, as well as cells or infectious disease-causing organisms or agents that are at least capable of binding to an antibody and preferably are also capable of stimulating an immune response.

Administration of an antibody composition against an infectious agent as a monotherapy or in combination with chemotherapy results in elimination of infectious particles. A single administration of antibodies decreases the number of infectious particles generally 10 to 100 fold, more commonly more than 1000-fold. Similarly, antibody therapy in patients with a malignant disease employed as a monotherapy or in combination with chemotherapy reduces the number of malignant cells generally 10 to 100 fold, or more than 1000-fold. Therapy may be repeated over an extended amount of time to assure the complete elimination of infectious particles, malignant cells, etc. In some instances, therapy with antibody preparations will be continued for extended periods of time in the absence of detectable amounts of infectious particles or undesirable cells.

Similarly, the use of antibody therapy for the modulation of immune responses may consist of single or multiple administrations of therapeutic antibodies. Therapy may be continued for extended periods of time in the absence of any disease symptoms.

Combination therapies are also contemplated. The subject pharmaceutical compositions may be administered coincident with at least one other therapeutic agent, or administration may be done at different times. For example, the subject treatment may be employed in conjunction with chemotherapy at dosages sufficient to inhibit infectious disease or malignancies. In autoimmune disease patients or transplant recipients, antibody therapy may be employed in conjunction with immunosuppressive therapy at dosages sufficient to inhibit immune reactions.

All citations are expressly incorporated herein in their entirety by reference.

EXPERIMENTAL

I. Meganuclease Design for Ig Target Sites

Directed Evolution of Homing Endonucleases Specific for Rat Immunoglobulin Sequences.

An analysis of rat IgM exon sequences resulted in the identification of several target cleavage sequences for engineered homing endonucleases. Using homing endonuclease I-SceI, two target sequences were identified, one within rat IgM exon II (CGTGGATCACAGGGGTCT) (SEQ ID NO: 1) and the other within rat IgM exon III (CTGGGATAACAG-GAAGGA) (SEQ ID NO: 2). These sites share 61% (11 out of 18 bases) sequence identity with the natural recognition sequence of I-SceI (TAGGGATAACAGGGTAAT) (SEQ ID NO: 3).

TABLE 1

Target sequences in rat IgM exons
the different nucleotides are underlined)

| Target | Sequence | Similarity | position |
|---|---|---|---|
| T3 | CGTGGATCACAGGGGTCT | 61% | Exon II |
|  | SEQ ID NO: 1 |  |  |
| T4 | CTGGGATAACAGGAAGGA | 61% | Exon III |
|  | SEQ ID NO: 2 |  |  |
| Wild type | TAGGGATAACAGGGTAAT SEQ ID NO: 3 |  |  |

For the engineering of homing endonucleases specific for these target sequences we used a highly sensitive selection for the directed evolution of homing endonucleases that couples enzymatic DNA cleavage with the survival of host cells (described in detail by Chen and Zhao, Nucleic Acid Research 33(18):e154, 2005). An in vitro coevolution strategy was used to engineer I-SceI variants with target sequence specificity. As shown in Table 2, for target sequence T3, two new sequences, T3 i1 and T3i2, were selected as intermediate sequences, while for target sequence T4, two new sequences, T4 μl and T4i2, were selected as intermediate sequences. The T3i1 and T4 i1 sequences were cloned into the report plasmid to yield p11-LacY-T3i1 and p11-LacY-T4 i1, respectively.

TABLE 2

Sequences in three steps (the different nucleotides are underlined)

| Step1 | T3i1 | TAGGGATAA CAGGGGTCT | T4i1 | TAGGGATAA CAGGGAAGGA |
|---|---|---|---|---|
|  |  | SEQ ID NO: 4 |  | SEQ ID NO: 6 |

TABLE 2-continued

Sequences in three steps (the different
nucleotides are underlined)

| Step2 | T3i2 | CGTGGATAA CAGGGGTCT | T4i2 | CTGGGATAA CAGGAAGGA |
|---|---|---|---|---|
| | | SEQ ID NO: 5 | | SEQ ID NO: 2 |
| Step3 | T3 | CGTGGATCA CAGGGGTCT | T4 | CTGGGATAA CAGGAAGGA |
| | | SEQ ID NO: 1 | | SEQ ID NO: 2 |

Figure 2:
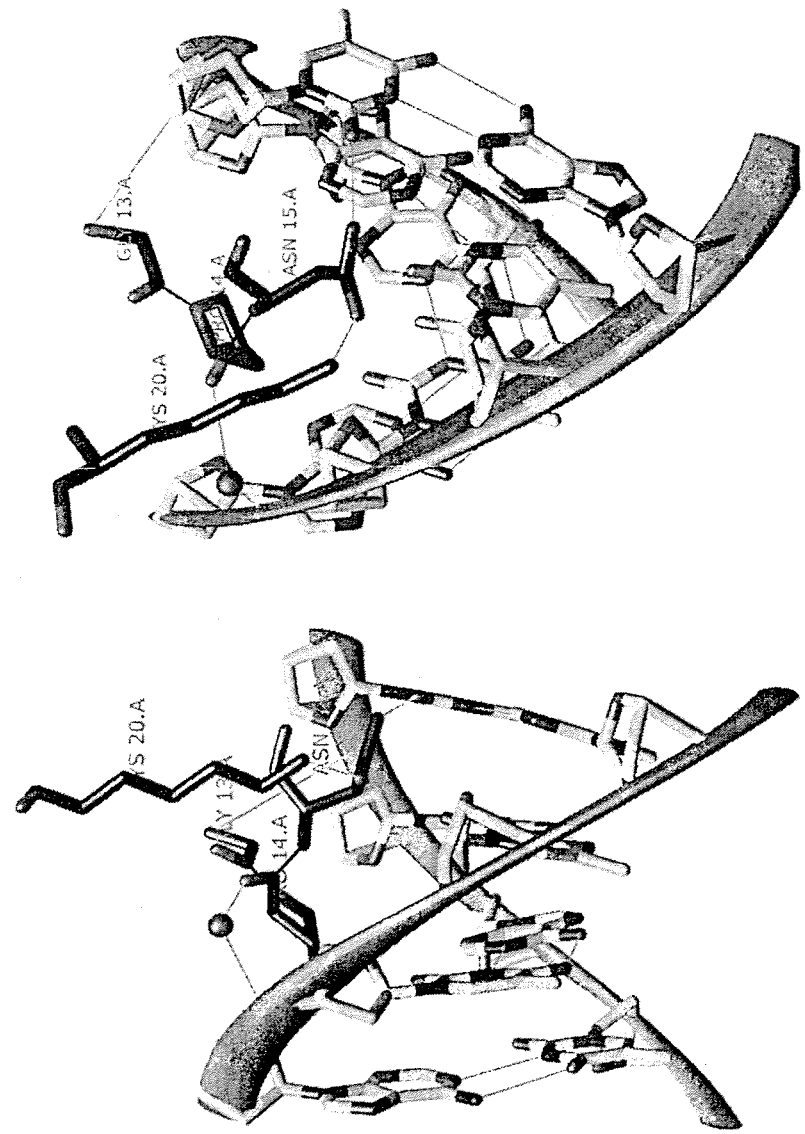
FIG. 2. Schematic of the interaction of I-SceI and DNA at 3' end of recognition sequence.
Figure 3:
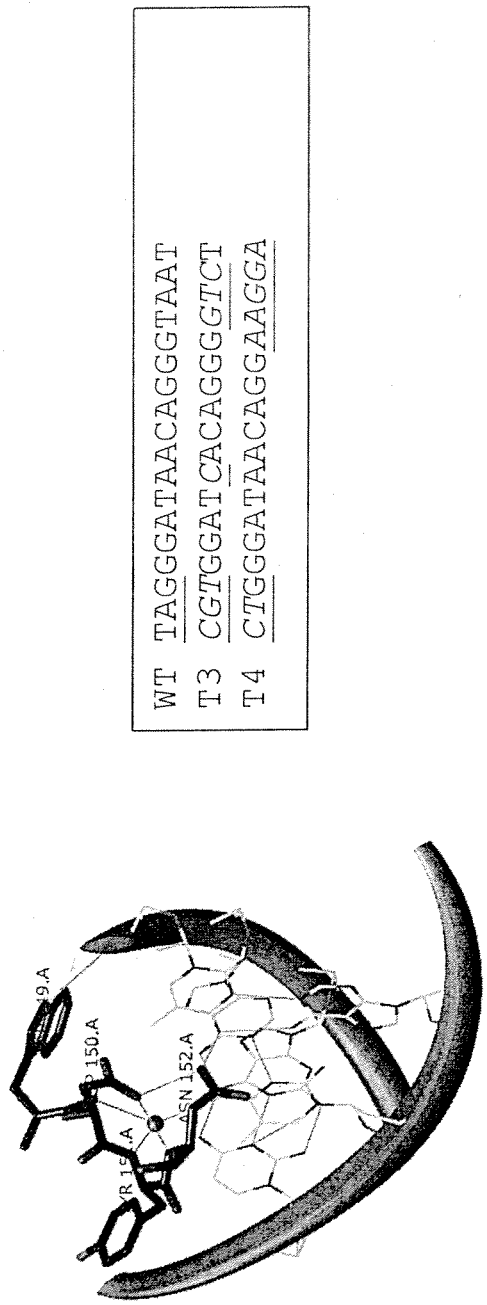
FIG. 3. Schematic of the interaction of the 5' end of the I-SceI recognition sequence with I-Sce, wherein WT is SEQ ID NO: 3; T3 is SEQ ID NO: 1 and T4 is SEQ .I.D. NO. 2.

To obtain I-SceI mutants with T3i1 or T4 μ1 sequence specificity, molecular modeling was first carried out to identify the residues to be used to create a focused library via saturation mutagenesis. As shown in FIG. 2, I-SceI binds to the 3' end of T3 μl or T4i1 through a relaxed loop that lies in the minor groove of DNA. Residues Gly13, Pro14, Asn15 and Lys20 are close to this 3' end and Asn15 binds directly to the last thymine at the 3' end of the wild type recognition sequence through hydrogen bonds. A library of mutants containing all the possible combinations of amino acid substitutions at these four select residues were constructed by saturation mutagenesis. To generate a large enough library, the ligation reaction and DNA transformation procedures were optimized through several trials. A library consisting of 2.9× $10^6$ mutants was created.

The library was screened for I-SceI mutants with increased activity towards the T3 μl sequence. Compared to round 0 (wild type I-SceI), the first round of screening yielded mutants with increased activity toward the T3 μl sequence since the cell survival rate was increased by 10-fold. Enrichment of the potentially positive mutants in round 2 and 3 showed further improvement in cell survival rate. Similarly, the library was screened for I-SceI mutants with increased activity towards the T4 μl sequence. Screening of mutants yielded mutants with increased activity toward the T4i1 sequence.

In parallel, a second library of I-SceI mutants targeting the 5' end of the recognition sequence was designed. The first library created using saturation mutagenesis was focused on those residues interacting with the 3' end of the four nucleotides of the I-SceI recognition sequence. Based on molecular modeling, Trp149, Asp150, Tyr151 and Asn152 lie in the major groove formed by the 5' end nucleotides. Asn152 interacts directly with T(−7) though hydrogen bonding. Asp150 and Tyr152 interact T opposite to A(−6) indirectly though a water molecule. Trp149 and Tyr151 interact with the phosphate backbone. Thus these four residues are important in the sequence specificity of I-SceI and simultaneous saturation mutagenesis on these four residues was done to create a second I-SceI mutant library.

Further coevolution of these enzymes results in the generation of novel meganucleases specific for target sequences in rat IgM exons II and III (CGTGGATCACAGGGGTCT (SEQ ID NO: 1) and CTGGGATAACAGGAAGGA (SEQ ID NO: 2)).

Engineering of I-Cre with Defined Sequence Specificity

Figure 4:
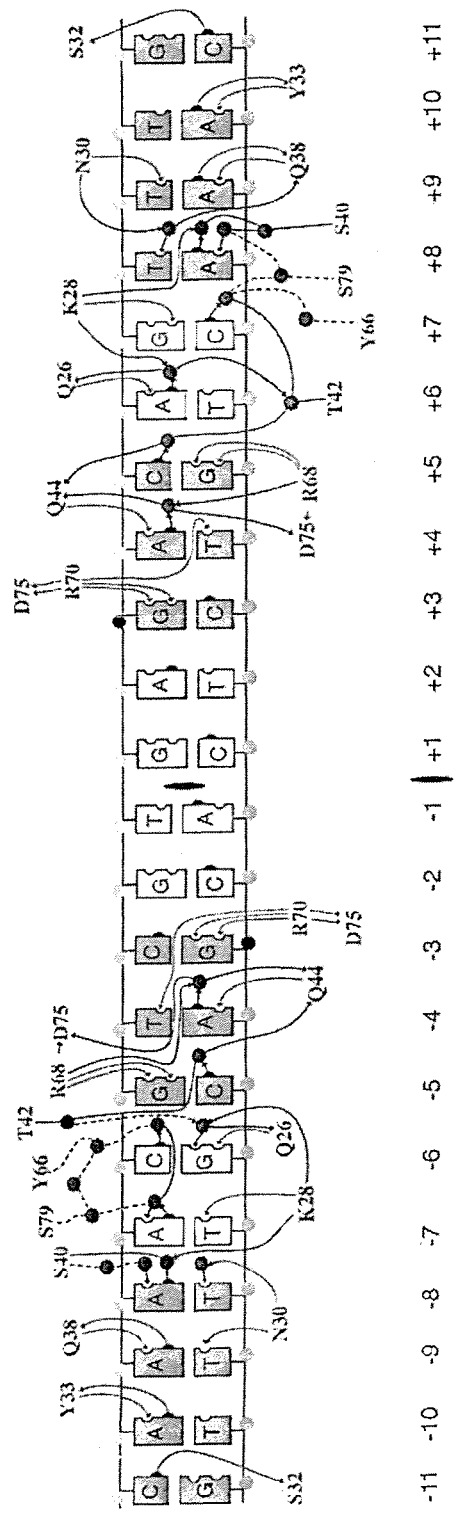
FIG. 4. Schematic of sequence recognition mechanism of I-CreI (from Nucleic Acids Res., 34, 4791-4800), wherein the first sequence is SEQ ID NO: 8 and the second sequence is SEQ ID NO: 58.
Figure 5:
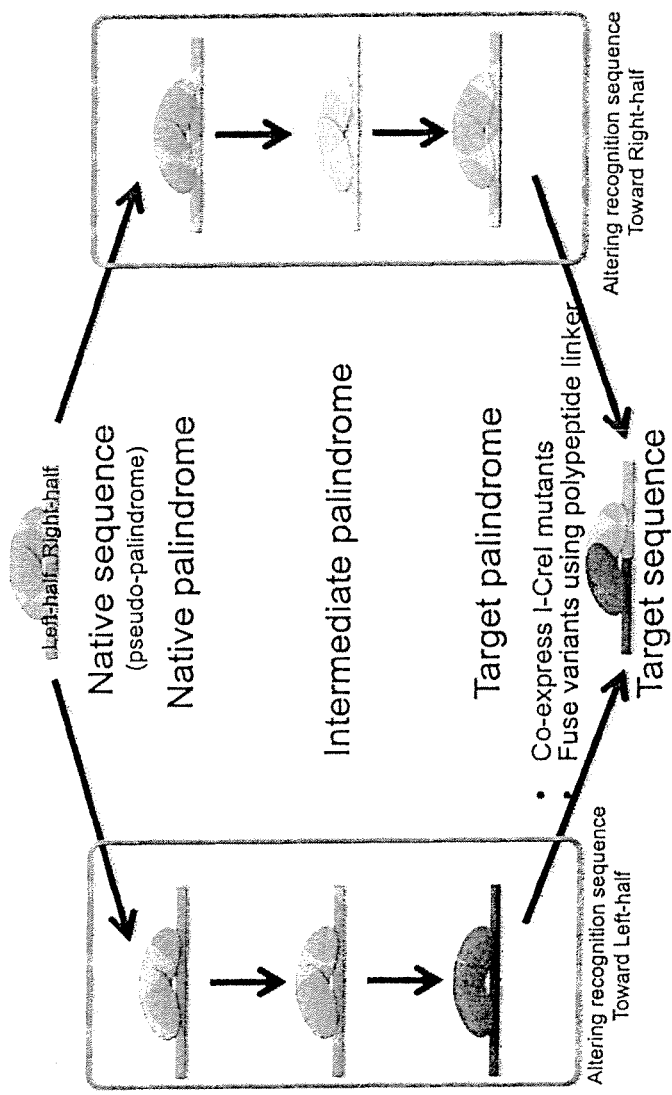
FIG. 5. Schematic diagram of the strategy for altering recognition sequence of I-CreI.

For the engineering of homing endonucleases specific for novel target sequences we used a highly sensitive selection for the directed evolution of homing endonucleases that couples enzymatic DNA cleavage with the survival of host cells (described in detail by Chen and Zhao, Nucleic Acid Research 33(18):e154, 2005). In addition, a general strategy for engineering I-CreI mutant with defined sequence specificity was designed. I-CreI recognizes a target sequence in a pseudo palindromic manner. Palindromic bases are directly recognized by I-CreI and may be difficult to be altered (J. Mol. Biol., 280, 345-353) (FIG. 4).

This property hinders the direct engineering of I-CreI derivatives that recognize a non-palindromic sequence. To overcome this problem, the target sequence was divided into left-half (upstream-half) and right-half (downstream-half). I-CreI is optimized for the intermediate sequences of the left-half palindrome and the right-half palindrome, respectively (FIG. 4). Then, the I-CreI mutants, optimized for intermediate sequences, are engineered to recognize the target sequence palindrome. Finally. I-CreI mutant respectively optimized for left-half and that for right-half will be co-expressed to cleave the target sequence. In addition, fusion of the left-half optimized mutant with the right-half optimized mutant by a polypeptide linker is examined.

A target sequence within exon IV (CAACTGATCCT-GAGGGAGTCGG) (SEQ ID NO: 7) that shares 59% sequence identity with the natural recognition sequence of homing endonuclease I-CreI was identified. Subsequently, based on the identity of palindromic bases within the original ICreI target sequence, two sequences, T5 and T6, were selected as target sequences for I-CreI engineering.

TABLE 3

I-CreI recognition sequence and 2 target sequences

| | -11 | -10 | -9 | -8 | -7 | -6 | -5 | -4 | -3 | -2 | -1 | 1 | 2 | 3 | 4 | 5 | 6 | 7 | 8 | 9 | 10 | 11 |
|---|---|---|---|---|---|---|---|---|---|---|---|---|---|---|---|---|---|---|---|---|---|---|
| | First half | | | | | | | | | | | Second half | | | | | | | | | | |
| Original *SID 9 | C | A | A | A | A | C | G | T | C | G | T | G | A | G | A | C | A | G | T | T | T | G |
| T5 *SID 9 | A | A | A | A | A | T | G | T | C | C | T | T | G | A | A | G | G | T | T | C | A | G |
| T6 *SID 7 | C | A | A | C | T | G | A | T | C | C | T | G | A | G | G | G | A | G | T | C | G | G |

*SID refers to SEQ ID NO:
Palindromic bases are highlighted.
Conserved bases are written in bold face.

| Original | Homology | |
|---|---|---|
| *SID 8 | Total | Palindromic |
| T5 *SID 9 | 50.0% | 64.3% |
| T6 *SID 7 | 59.1% | 57.1% |

*SID refers to SEQ ID NO:

The two target sequences, T5 and T6, were cloned into reporter plasmids. The I-CreI gene was cloned into the pTrc plasmid and sequenced to confirm that no mutations were introduced during PCR amplification. The I-CreI selection system is evaluated for cell survival rates.

In addition, molecular modeling was performed and protein residues that contact directly the DNA substrate were identified. In addition, we designed the intermediate sequences for in vitro co-evolution experiments.

TABLE 4

Target residues for saturation mutagenesis

| | Target residue |
|---|---|
| YN-TS5-L | Q26 and S32 |
| YN-TS5-Ri1 | R68, R70 and D75 |
| YN-TS5-Ri2 | Q26 and K28 |
| YN-TS5-Ri3 | N30, Y33 and Q38 |
| YN-TS6-L | Q26, K28 and R68 |
| YN-TS6-Ri1 | Q44 and R68 |
| YN-TS6-Ri2 | N30, Y33 and Q38 |

Subsequently, libraries of ICreI mutants are generated and screened for ICreI derivatives with novel target sequences. Further coevolution of these enzymes results in the generation of novel meganucleases specific for a target sequence within exon IV of rat IgM (CAACTGATCCTGAGG-GAGTCGG) (SEQ ID NO: 7).

Engineering of Zinc-Finger Nucleases

Zinc-finger proteins (ZFP) were designed against sequences encoding rat IgM (exons 1-4) and assembled as described (Zhang, L. et al. Synthetic zing finger transcription factor action at an endogenous chromosomal site. Activation of the human erythropoietin gene. J. Biol. Chem 275:33850-33860, 2000, and Liu, P. Q. et al. Regulation of an endogenous locus against a panel of designed zinc finger proteins targeted to accessible chromatin regions. Activation of vascular endothelial growth factor. J. Biol. Chem. 2765:11323-11334, 2001), to yield the following ZFP moieties.

Figure 6:
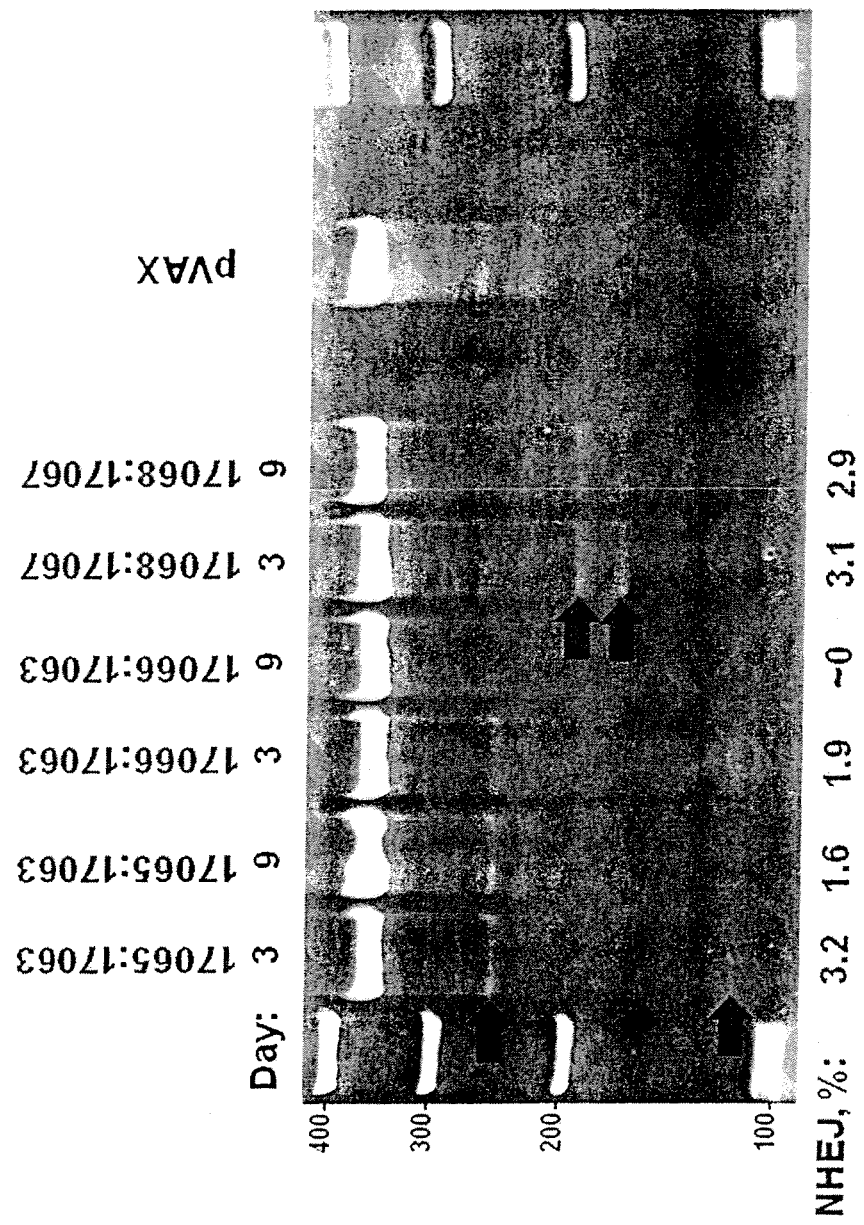
FIG. 6. Zinc-finger proteins (ZFP) designed against sequences encoding rat IgM were expressed in cells, chromosomal DNA was prepared, and the appropriate region of the IgM locus was PCR amplified. Reaction products were analyzed by polyacrylamide gel electrophoresis. The figure shows a typical example demonstrating cleavage activity.

(FCS, Hyclone), 15% horse serum (Invitrogen) and 5 mM glutamine. Cells were disassociated from plasticware using TrypLE Select protease (Invitrogen). For transfection, 200,000 C6 cells were mixed with 400 ng plamid DNA and 20 µL Amaxa Solution SF. Cells were transfected in an Amaxa Nucleofector II Shuttle using program 96 FF-137 and recovered into 0.1 L warm, supplemented, F-12 medium. Three and nine days post transfection cells were harvested and chromosomal DNA was prepared using a Quick Extract Solution 1.0 (Epicentre). The appropriate region of the IgM locus was PCR amplified using Accuprime High-fidelity DNA polymerase (Invitrogen). PCR reactions were heated to 94°, then gradually cooled to room temperature. Approximately 200 ng of the annealed DNA was mixed with 0.33 µL CEL-I enzyme (Transgenomic) and incubated for 20 minutes at 42°. Reaction products were analyzed by polyacrylamide gel electrophoresis in 1×Tris-borate-EDTA buffer. A typical example demonstrating cleavage activity is shown in FIG. 6.

II. IgM Exon Replacement by Homologous Recombination

Replacement of Rat IgM CH1 with Human IgM CH1 by Homologous Recombination in Rat Embryos BAC clone N12 containing part of the rat immunoglobulin locus including IgM exons was modified by homologous recombination in E coli. In the resulting BAC clone pN12CH1hu the exon encoding rat IgM CH1 is replaced with an exon encoding human IgM CH1. For the replacement of the exon encoding rat IgM CH1 with an exon encoding human IgM CH1 by homologous recombination in embryos, a donor DNA fragment was constructed as follows: The BstEll fragment (2639 bp) containing human CH1 was isolated from pN12CH1hu, cloned into pBluescript SK+ and purified by Maxi Qiagen endofree kit.

TABLE 5

| SBS | SBS Recognition sequence Recognition sequence | Finger 1 | Finger 2 | Finger 3 | Finger 4 | Finger 5 | Finger 6 | Linker 2-3 | Linker 4-5 |
|---|---|---|---|---|---|---|---|---|---|
| 17063 | AGAGAGGGGGCTCTC SID 10 | NKVGLIE SID 11 | TSSDLSR SID 12 | RSDHLSR SID 13 | RSDNLSE SID 14 | QNAHRKT SID 15 | | TGGERP SID 16 | TGEKP SID 17 |
| 17065 | AATTTGGTGGCCATG SID 18 | RSDALST SID 19 | DRSTRTK SID 20 | RSDALAR SID 21 | RSDSLSA SID 22 | TSSNRKT SID 23 | | TGGQRP SID 24 | TGEKP SID 17 |
| 17067 | GTTCTGGTAGTT SID 25 | RSANLAR SID 26 | RSDNLRE SID 27 | TSGSLSR SID 28 | QSGSLTR SID 29 | RSDVLSE SID 30 | | TGGGGSQRP SID 31 | TGSQKP SID 32 |
| 17068 | GAAGTCATGCAGGGTGTC SID 33 | DRSALSR SID 34 | TSGHLSR SID 35 | RSDNLST SID 36 | HNATRIN SID 37 | DRSALSR SID 34 | TSGSLTR SID 38 | TGGQRP SID 24 | TGSQKP SID 32 |
| 17080 | GGTGCCATTGGGGTG SID 39 | RSDALAR SID 21 | RSDHLST SID 40 | HSNARKN SID 41 | ERGTLAR SID 42 | TSGHLSR SID 35 | QSGNLAR SID 43 | TGEKP SID 17 | TGSQKP SID 32 |
| 17060 | GCTGTGGGTGTGGCT SID 44 | QSSDLSR SID 45 | RSDALTQ SID 46 | TSGHLSR SID 35 | RSDALSR SID 47 | DRSDLSR SID 48 | | TGGQRP SID 24 | TGEKP SID 17 |
| 17119 | ACCATGTGTGGCAGGG SID 49 | RSAHLSR SID 50 | QSGDLTR SID 51 | RSDALAR SID 21 | RSDTLSV SID 52 | DNSTRIK SID 53 | | TGEKP SID 17 | TGEKP SID 17 |
| 17120 | GAGGACCGTGGACAAG SID 54 | RSANLSV SID 55 | DRANLSR SID 56 | RSDALAR SID 21 | DRSDLSR SID 48 | RSDDLTR SID 57 | | TGEKP SID 17 | TGEKP SID 17 |

(* SID represents SEQ ID NO:)

DNA encoding ZFPs ere cloned into an expression vector. Rat C6 cells were obtained from the American Type Culture Collection and grown as recommended in F-12 medium (Invitrogen) supplemented with 5% qualified fetal calf serum For the induction of double-strand breaks within the rat IgM CH1 exon a zinc-finger-nuclease was designed. Injection of mRNA (2 ng/ul) encoding this ZFN and donor plasmid DNA (4 ng/ul) into pronuclei of fertilized rat oocytes and subsequent transfer into foster mother animals resulted in the birth of 84 rats. In 8 of these 84 animals injection of mRNA and donor plasmid DNA resulted in short deletions in the rat IgM CH1 exon in the animal's genome but not in replacement of rat IgM CH1 exon with human IgM CH1 exon. In 2 of the 84 animals homologous recombination was detected by PCR.

Replacement of the rat IgM CH1 exon with human IgM CH1 exon in mutant animals was demonstrated by PCR using the following primers:

rBstEllUp 5'-ACTGGGATAAACTGGGCTAAAC-3' combined with huCH1Lo 5'-GATGGAGTCGGGAAG-GAAGT-3', or rBstEllLo 5'-GCATCGGACAATCAAAAC-CAGTG-3' with 5CH1 huUp 5'-CAACTCTGACATCAG-CAGCACCC-3'.

Replacement of rat IgM CH1 exon with human IgM CH1 exon was confirmed by Southern-blot.

The invention claimed is:

1. A method for integrating an exogenous nucleic acid sequence into an endogenous immunoglobulin (Ig) gene of a rodent embryo, comprising
   introducing a meganuclease into said rodent embryo, wherein said meganuclease causes a chromosomal break in genomic DNA of said embryo at a cleavage site located within 1.5 kb of said Ig gene, and
   introducing into said rodent embryo an exogenous nucleic acid sequence, wherein said exogenous nucleic acid sequence comprises an insertion sequence flanked by two homology arms such that said insertion sequence is integrated into said genomic DNA at said endogenous Ig gene by homologous recombination.

2. The method according to claim 1, wherein said rodent embryo is a single cell fertilized oocyte.

3. The method according to claim 1, wherein said insertion sequence is homologous to an exon of said endogenous Ig gene.

4. The method according to claim 3, wherein said insertion sequence comprises a human Ig exon.

5. The method according to claim 3, wherein said endogenous Ig gene comprises an Ig gene segment selected from the group consisting of a rodent variable (V) gene segment, a rodent diversity (D) gene segment, a rodent joining (J) gene segment, and a rodent constant (C) gene segment.

6. The method according to claim 1, wherein said insertion sequence comprises a nucleotide sequence selected from the group consisting of a human variable (V) Ig segment, a human diversity (D) Ig segment, a human joining (J) Ig segment, a human constant (C) Ig segment, and portions thereof.

7. The method according to claim 6, wherein said insertion sequence comprises a human V gene segment.

8. The method according to claim 1, wherein said insertion sequence introduces a deletion into said endogenous Ig gene.

9. The method according to claim 1, wherein said insertion sequence introduces a stop codon into said endogenous Ig gene.

10. The method according to claim 1, wherein said insertion sequence disrupts said endogenous Ig gene.

* * * * *

SEQUENCE LISTING

<160> NUMBER OF SEQ ID NOS: 58

<210> SEQ ID NO 1
<211> LENGTH: 18
<212> TYPE: DNA
<213> ORGANISM: Rattus rattus

<400> SEQUENCE: 1
cgtggatcac agggtct                                                          18

<210> SEQ ID NO 2
<211> LENGTH: 18
<212> TYPE: DNA
<213> ORGANISM: Rattus rattus

<400> SEQUENCE: 2
ctgggataac aggaagga                                                         18

<210> SEQ ID NO 3
<211> LENGTH: 18
<212> TYPE: DNA
<213> ORGANISM: Rattus rattus

<400> SEQUENCE: 3
tagggataac agggtaat                                                         18

<210> SEQ ID NO 4
<211> LENGTH: 18
<212> TYPE: DNA
<213> ORGANISM: Artificial Sequence
<220> FEATURE:
<223> OTHER INFORMATION: Synthetic

<400> SEQUENCE: 4
tagggataac agggtct                                                          18

<210> SEQ ID NO 5
<211> LENGTH: 18
<212> TYPE: DNA
<213> ORGANISM: Artificial Sequence
<220> FEATURE:
<223> OTHER INFORMATION: Synthetic

<400> SEQUENCE: 5
cgtggataac agggtct                                                          18

<210> SEQ ID NO 6
<211> LENGTH: 18
<212> TYPE: DNA
<213> ORGANISM: Artificial Sequence
<220> FEATURE:
<223> OTHER INFORMATION: Synthetic

<400> SEQUENCE: 6
tagggataac agggagga                                                         18

<210> SEQ ID NO 7
<211> LENGTH: 22
<212> TYPE: DNA
<213> ORGANISM: Rattus rattus

<400> SEQUENCE: 7
caactgatcc tgagggagtc gg                                             22

<210> SEQ ID NO 8
<211> LENGTH: 22
<212> TYPE: DNA
<213> ORGANISM: Rattus rattus

<400> SEQUENCE: 8
caaaacgtcg tgagacagtt tg                                             22

<210> SEQ ID NO 9
<211> LENGTH: 22
<212> TYPE: DNA
<213> ORGANISM: Rattus rattus

<400> SEQUENCE: 9
aaaaatgtcc ttgaaggttc ag                                             22

<210> SEQ ID NO 10
<211> LENGTH: 15
<212> TYPE: DNA
<213> ORGANISM: Rattus rattus

<400> SEQUENCE: 10
agacaggggg ctctc                                                     15

<210> SEQ ID NO 11
<211> LENGTH: 7
<212> TYPE: PRT
<213> ORGANISM: Rattus rattus

<400> SEQUENCE: 11

Asn Lys Val Gly Leu Ile Glu
1               5

<210> SEQ ID NO 12
<211> LENGTH: 7
<212> TYPE: PRT
<213> ORGANISM: Rattus rattus

<400> SEQUENCE: 12

Thr Ser Ser Asp Leu Ser Arg
1               5

<210> SEQ ID NO 13
<211> LENGTH: 7
<212> TYPE: PRT
<213> ORGANISM: Rattus rattus

<400> SEQUENCE: 13

Arg Ser Asp His Leu Ser Arg
1               5

<210> SEQ ID NO 14
<211> LENGTH: 7
<212> TYPE: PRT
<213> ORGANISM: Rattus rattus

<400> SEQUENCE: 14

Arg Ser Asp Asn Leu Ser Glu
1               5

<210> SEQ ID NO 15
<211> LENGTH: 7
<212> TYPE: PRT
<213> ORGANISM: Rattus rattus

<400> SEQUENCE: 15

Gln Asn Ala His Arg Lys Thr
1               5

<210> SEQ ID NO 16
<211> LENGTH: 6
<212> TYPE: PRT
<213> ORGANISM: Rattus rattus

<400> SEQUENCE: 16

Thr Gly Gly Glu Arg Pro
1               5

<210> SEQ ID NO 17
<211> LENGTH: 5
<212> TYPE: PRT
<213> ORGANISM: Rattus rattus

<400> SEQUENCE: 17

Thr Gly Glu Lys Pro
1               5

<210> SEQ ID NO 18
<211> LENGTH: 15
<212> TYPE: DNA
<213> ORGANISM: Rattus rattus

<400> SEQUENCE: 18
aatttggtgg ccatg                                                    15

<210> SEQ ID NO 19
<211> LENGTH: 7
<212> TYPE: PRT
<213> ORGANISM: Rattus rattus

<400> SEQUENCE: 19

Arg Ser Asp Ala Leu Ser Thr
1               5

<210> SEQ ID NO 20
<211> LENGTH: 7
<212> TYPE: PRT
<213> ORGANISM: Rattus rattus

<400> SEQUENCE: 20

Asp Arg Ser Thr Arg Thr Lys
1               5

<210> SEQ ID NO 21
<211> LENGTH: 7
<212> TYPE: PRT
<213> ORGANISM: Rattus rattus

<400> SEQUENCE: 21

Arg Ser Asp Ala Leu Ala Arg
1               5

<210> SEQ ID NO 22
<211> LENGTH: 7
<212> TYPE: PRT
<213> ORGANISM: Rattus rattus

<400> SEQUENCE: 22

Arg Ser Asp Ser Leu Ser Ala
1               5

<210> SEQ ID NO 23
<211> LENGTH: 7
<212> TYPE: PRT
<213> ORGANISM: Rattus rattus

<400> SEQUENCE: 23

Thr Ser Ser Asn Arg Lys Thr
1               5

<210> SEQ ID NO 24
<211> LENGTH: 6
<212> TYPE: PRT
<213> ORGANISM: Rattus rattus

<400> SEQUENCE: 24

Thr Gly Gly Gln Arg Pro
1               5

<210> SEQ ID NO 25
<211> LENGTH: 12
<212> TYPE: DNA
<213> ORGANISM: Rattus rattus

<400> SEQUENCE: 25
gttctggtag tt                                                            12

<210> SEQ ID NO 26
<211> LENGTH: 7
<212> TYPE: PRT
<213> ORGANISM: Rattus rattus

<400> SEQUENCE: 26

Arg Ser Ala Asn Leu Ala Arg
1               5

<210> SEQ ID NO 27
<211> LENGTH: 7
<212> TYPE: PRT
<213> ORGANISM: Rattus rattus

<400> SEQUENCE: 27

Arg Ser Asp Asn Leu Arg Glu
1               5

<210> SEQ ID NO 28
<211> LENGTH: 7
<212> TYPE: PRT
<213> ORGANISM: Rattus rattus

<400> SEQUENCE: 28

Thr Ser Gly Ser Leu Ser Arg
1               5

```
<210> SEQ ID NO 29
<211> LENGTH: 7
<212> TYPE: PRT
<213> ORGANISM: Rattus rattus

<400> SEQUENCE: 29

Gln Ser Gly Ser Leu Thr Arg
1               5

<210> SEQ ID NO 30
<211> LENGTH: 7
<212> TYPE: PRT
<213> ORGANISM: Rattus rattus

<400> SEQUENCE: 30

Arg Ser Asp Val Leu Ser Glu
1               5

<210> SEQ ID NO 31
<211> LENGTH: 9
<212> TYPE: PRT
<213> ORGANISM: Rattus rattus

<400> SEQUENCE: 31

Thr Gly Gly Gly Gly Ser Gln Arg Pro
1               5

<210> SEQ ID NO 32
<211> LENGTH: 6
<212> TYPE: PRT
<213> ORGANISM: Rattus rattus

<400> SEQUENCE: 32

Thr Gly Ser Gln Lys Pro
1               5

<210> SEQ ID NO 33
<211> LENGTH: 18
<212> TYPE: DNA
<213> ORGANISM: Rattus rattus

<400> SEQUENCE: 33
gaagtcatgc agggtgtc                                                   18

<210> SEQ ID NO 34
<211> LENGTH: 7
<212> TYPE: PRT
<213> ORGANISM: Rattus rattus

<400> SEQUENCE: 34

Asp Arg Ser Ala Leu Ser Arg
1               5

<210> SEQ ID NO 35
<211> LENGTH: 7
<212> TYPE: PRT
<213> ORGANISM: Rattus rattus

<400> SEQUENCE: 35

Thr Ser Gly His Leu Ser Arg
1               5

<210> SEQ ID NO 36
<211> LENGTH: 7
```

```
<212> TYPE: PRT
<213> ORGANISM: Rattus rattus

<400> SEQUENCE: 36

Arg Ser Asp Asn Leu Ser Thr
1               5

<210> SEQ ID NO 37
<211> LENGTH: 7
<212> TYPE: PRT
<213> ORGANISM: Rattus rattus

<400> SEQUENCE: 37

His Asn Ala Thr Arg Ile Asn
1               5

<210> SEQ ID NO 38
<211> LENGTH: 7
<212> TYPE: PRT
<213> ORGANISM: Rattus rattus

<400> SEQUENCE: 38

Thr Ser Gly Ser Leu Thr Arg
1               5

<210> SEQ ID NO 39
<211> LENGTH: 15
<212> TYPE: DNA
<213> ORGANISM: Rattus rattus

<400> SEQUENCE: 39
ggtgccattg gggtg                                                    15

<210> SEQ ID NO 40
<211> LENGTH: 7
<212> TYPE: PRT
<213> ORGANISM: Rattus rattus

<400> SEQUENCE: 40

Arg Ser Asp His Leu Ser Thr
1               5

<210> SEQ ID NO 41
<211> LENGTH: 7
<212> TYPE: PRT
<213> ORGANISM: Rattus rattus

<400> SEQUENCE: 41

His Ser Asn Ala Arg Lys Asn
1               5

<210> SEQ ID NO 42
<211> LENGTH: 7
<212> TYPE: PRT
<213> ORGANISM: Rattus rattus

<400> SEQUENCE: 42

Glu Arg Gly Thr Leu Ala Arg
1               5

<210> SEQ ID NO 43
<211> LENGTH: 7
<212> TYPE: PRT
<213> ORGANISM: Rattus rattus
```

<400> SEQUENCE: 43

Gln Ser Gly Asn Leu Ala Arg
1               5

<210> SEQ ID NO 44
<211> LENGTH: 15
<212> TYPE: DNA
<213> ORGANISM: Rattus rattus

<400> SEQUENCE: 44
gctgtgggtg tggct                                              15

<210> SEQ ID NO 45
<211> LENGTH: 7
<212> TYPE: PRT
<213> ORGANISM: Rattus rattus

<400> SEQUENCE: 45

Gln Ser Ser Asp Leu Ser Arg
1               5

<210> SEQ ID NO 46
<211> LENGTH: 7
<212> TYPE: PRT
<213> ORGANISM: Rattus rattus

<400> SEQUENCE: 46

Arg Ser Asp Ala Leu Thr Gln
1               5

<210> SEQ ID NO 47
<211> LENGTH: 7
<212> TYPE: PRT
<213> ORGANISM: Rattus rattus

<400> SEQUENCE: 47

Arg Ser Asp Ala Leu Ser Arg
1               5

<210> SEQ ID NO 48
<211> LENGTH: 7
<212> TYPE: PRT
<213> ORGANISM: Rattus rattus

<400> SEQUENCE: 48

Asp Arg Ser Asp Leu Ser Arg
1               5

<210> SEQ ID NO 49
<211> LENGTH: 16
<212> TYPE: DNA
<213> ORGANISM: Rattus rattus

<400> SEQUENCE: 49
accatgtgtg gcaggg                                             16

<210> SEQ ID NO 50
<211> LENGTH: 7
<212> TYPE: PRT
<213> ORGANISM: Rattus rattus

<400> SEQUENCE: 50

Arg Ser Ala His Leu Ser Arg
1               5

<210> SEQ ID NO 51
<211> LENGTH: 7
<212> TYPE: PRT
<213> ORGANISM: Rattus rattus

<400> SEQUENCE: 51

Gln Ser Gly Asp Leu Thr Arg
1               5

<210> SEQ ID NO 52
<211> LENGTH: 7
<212> TYPE: PRT
<213> ORGANISM: Rattus rattus

<400> SEQUENCE: 52

Arg Ser Asp Thr Leu Ser Val
1               5

<210> SEQ ID NO 53
<211> LENGTH: 7
<212> TYPE: PRT
<213> ORGANISM: Rattus rattus

<400> SEQUENCE: 53

Asp Asn Ser Thr Arg Ile Lys
1               5

<210> SEQ ID NO 54
<211> LENGTH: 16
<212> TYPE: DNA
<213> ORGANISM: Rattus rattus

<400> SEQUENCE: 54
gaggaccgtg gacaag                                                     16

<210> SEQ ID NO 55
<211> LENGTH: 7
<212> TYPE: PRT
<213> ORGANISM: Rattus rattus

<400> SEQUENCE: 55

Arg Ser Ala Asn Leu Ser Val
1               5

<210> SEQ ID NO 56
<211> LENGTH: 7
<212> TYPE: PRT
<213> ORGANISM: Rattus rattus

<400> SEQUENCE: 56

Asp Arg Ala Asn Leu Ser Arg
1               5

<210> SEQ ID NO 57
<211> LENGTH: 7
<212> TYPE: PRT
<213> ORGANISM: Rattus rattus

<400> SEQUENCE: 57

Arg Ser Asp Asp Leu Thr Arg
1               5

```
<210> SEQ ID NO 58
<211> LENGTH: 22
<212> TYPE: DNA
<213> ORGANISM: Rattus rattus

<400> SEQUENCE: 58
gttttgcagc actctgtcaa ac                                              22
```